US012478099B2

(12) United States Patent
Fujinaga

(10) Patent No.: US 12,478,099 B2
(45) Date of Patent: Nov. 25, 2025

(54) POWER SUPPLY UNIT OF AEROSOL GENERATING DEVICE AND AEROSOL GENERATING DEVICE

(71) Applicant: Japan Tobacco Inc., Tokyo (JP)

(72) Inventor: Ikuo Fujinaga, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 366 days.

(21) Appl. No.: 18/070,486

(22) Filed: Nov. 29, 2022

(65) Prior Publication Data

US 2023/0086697 A1 Mar. 23, 2023

Related U.S. Application Data

(63) Continuation of application No. PCT/JP2021/044532, filed on Dec. 3, 2021.

(30) Foreign Application Priority Data

Dec. 4, 2020 (JP) ................................ 2020-202111

(51) Int. Cl.
*A24F 40/42* (2020.01)
*A61M 15/00* (2006.01)

(52) U.S. Cl.
CPC ........... *A24F 40/42* (2020.01); *A61M 15/009* (2013.01)

(58) Field of Classification Search
CPC .......... A24F 40/10; A24F 40/40; A24F 40/42; A24F 40/46
See application file for complete search history.

(56) References Cited

U.S. PATENT DOCUMENTS

2014/0261495 A1* 9/2014 Novak, III .............. A24F 40/40 392/386
2015/0223522 A1* 8/2015 Ampolini .............. B23P 21/004 324/750.01
2020/0000147 A1* 1/2020 Wu ......................... A24F 40/40
(Continued)

FOREIGN PATENT DOCUMENTS

| | | | |
|---|---|---|---|
| CA | 3112582 | A1 | 3/2020 |
| CN | 111096484 | A | 5/2020 |
| EP | 3871538 | A1 | 9/2021 |

(Continued)

OTHER PUBLICATIONS

Extended European Search Report issued Sep. 23, 2024 in corresponding European Patent Application No. 21900717.6, 9 pages.
(Continued)

*Primary Examiner* — Abdullah A Riyami
*Assistant Examiner* — Thang H Nguyen
(74) *Attorney, Agent, or Firm* — XSENSUS LLP

(57) ABSTRACT

A power supply unit of an aerosol generating device includes: an accommodating portion with a bottom and cylindrical shape, which is configured to accommodate a columnar cartridge that stores an aerosol source in a state in which the cartridge is rotatable 360 degrees in a circumferential direction of the cartridge. A rotation suppressing portion configured to generate a frictional force between the cartridge and the rotation preventing portion so as to suppress rotation of the cartridge in the circumferential direction is provided on a bottom portion of the accommodating portion.

19 Claims, 16 Drawing Sheets

(56) References Cited

U.S. PATENT DOCUMENTS

2021/0282459 A1* 9/2021 Yamaguchi ............. A24F 40/42

FOREIGN PATENT DOCUMENTS

JP 6552028 B1 7/2019
WO WO-2017001989 A1 * 1/2017 ............... A24D 1/02
WO WO-2020084796 A1 * 4/2020 ............. A24F 40/40

OTHER PUBLICATIONS

International Search Report and Written Opinion mailed on Jan. 25, 2022, received for PCT Application PCT/JP2021/044532, filed on Dec. 3, 2021, 8 pages including English Translation.
Chinese Office Action issued Mar. 29, 2025 in corresponding Chinese Patent Application No. 202180039386.5, 17 pages.
Chinese Office Action issued Aug. 14, 2025 in corresponding Chinese Patent Application No. 202180039386.5, 12 pages.

* cited by examiner

POWER SUPPLY UNIT OF AEROSOL GENERATING DEVICE AND AEROSOL GENERATING DEVICE

CROSS-REFERENCE TO RELATED APPLICATIONS

This is a continuation of International Application No. PCT/JP2021/044532 filed on Dec. 3, 2021, and claims priority from Japanese Patent Application No. 2020-202111 filed on Dec. 4, 2020, the entire contents of each are incorporated herein by reference.

SUMMARY

A power supply unit of an aerosol generating device according to an aspect of the present disclosure includes: an accommodating portion with a bottom and cylindrical shape, which is configured to accommodate a columnar cartridge that stores an aerosol source in a state in which the cartridge is rotatable 360 degrees in a circumferential direction of the cartridge, in which a rotation preventing portion configured to generate a frictional force between the cartridge and the rotation suppressing portion so as to suppress rotation of the cartridge in the circumferential direction is provided on a bottom portion of the accommodating portion.

According to the present disclosure, it is possible to provide an aerosol generating device capable of improving operability and preventing wear of members without using any positioning mechanism.

DESCRIPTION OF EMBODIMENTS

Hereinafter, a power supply unit of an aerosol generating device according to an embodiment of the present disclosure will be described. First, an aerosol inhaler that is an example of an aerosol generating device including the power supply unit according to the present embodiment will be described with reference to FIGS. 1 to 3.

(Aerosol Inhaler)

An aerosol inhaler 1 is an instrument that generates fragrant aerosol without combustion and through which the generated aerosol is inhaled. The aerosol inhaler 1 preferably has a size that fits in a hand, and has a substantially rectangular parallelepiped shape. It should be noted that the aerosol inhaler 1 may also have an egg shape, an elliptical shape, or the like. In the following description, three directions orthogonal to the aerosol inhaler having the substantially rectangular parallelepiped shape will be respectively referred to as an up-down direction, a front-rear direction, and a left-right direction in descending order of lengths. In addition, in the following description, a front side, a rear side, a left side, a right side, an upper side, and a lower side are defined as shown in FIGS. 1 to 3, and the front side is represented by Fr, the rear side is represented by Rr, the left side is represented by L, the right side is represented by R, the upper side is represented by U, and the lower side is represented by D for the sake of convenience.

Figure 1:
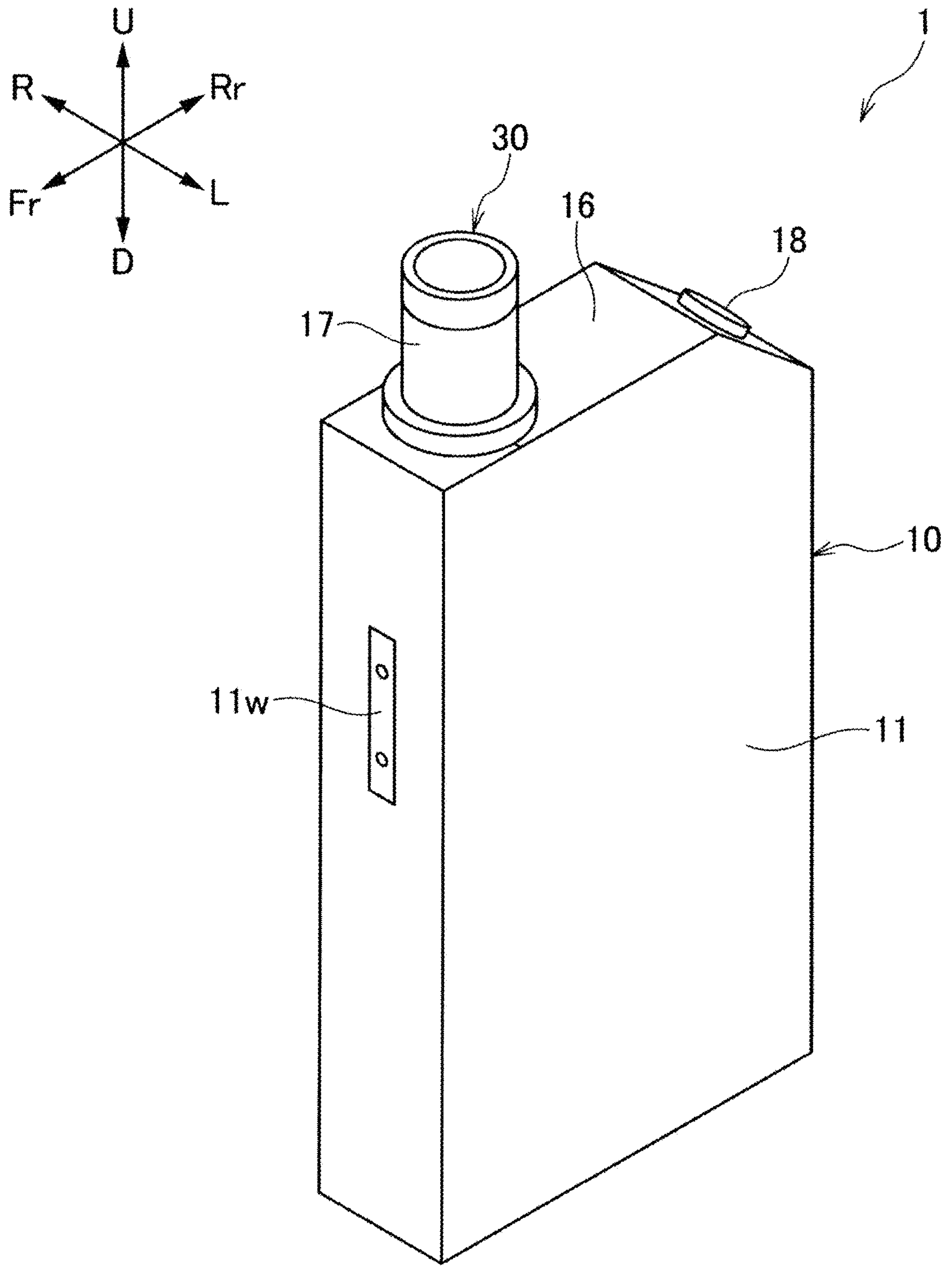
FIG. 1 is a perspective view of an aerosol inhaler according to an embodiment of the present disclosure.
Figure 2:
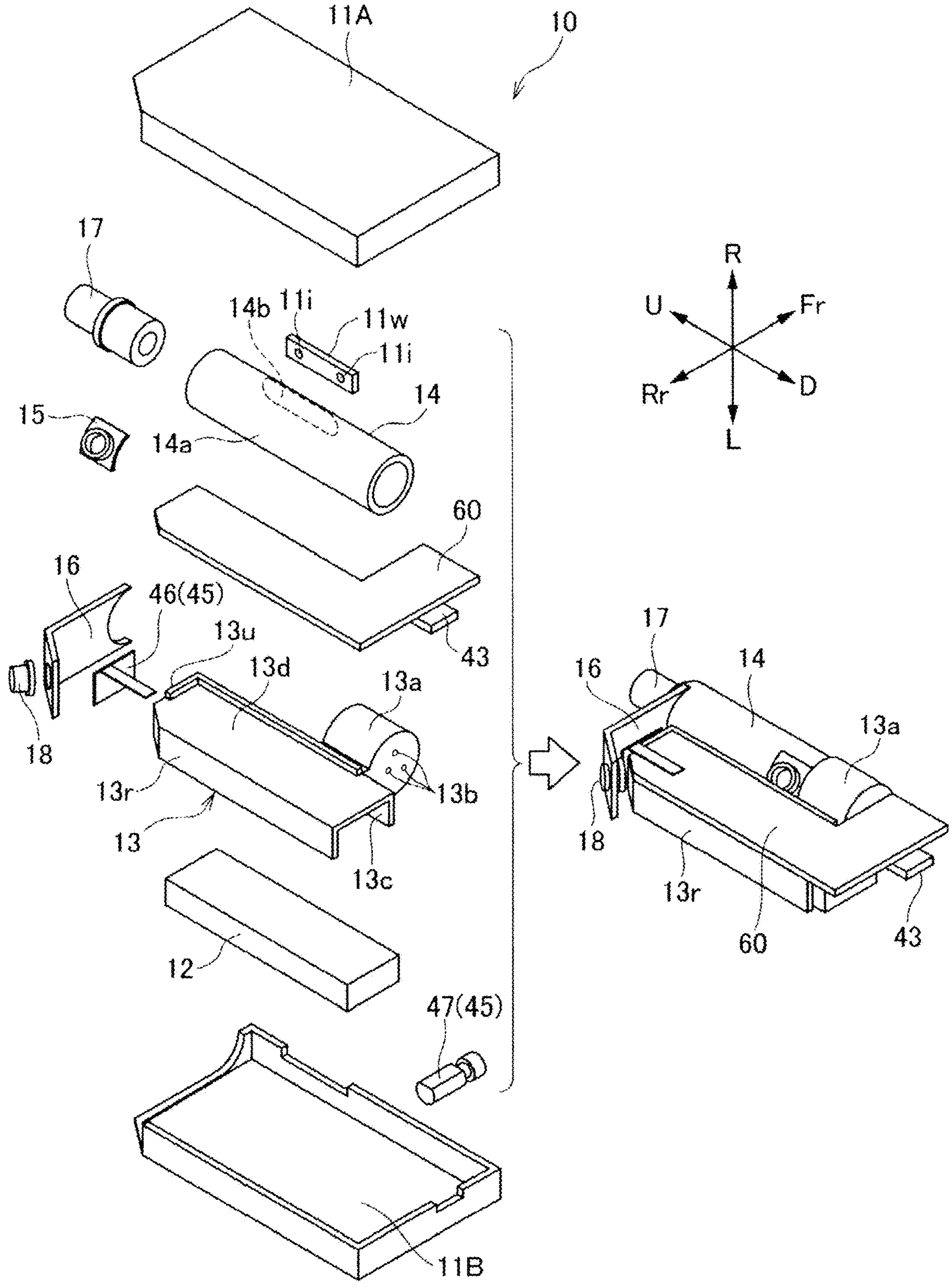
FIG. 2 is an exploded perspective view of the aerosol inhaler in FIG. 1.
Figure 3:
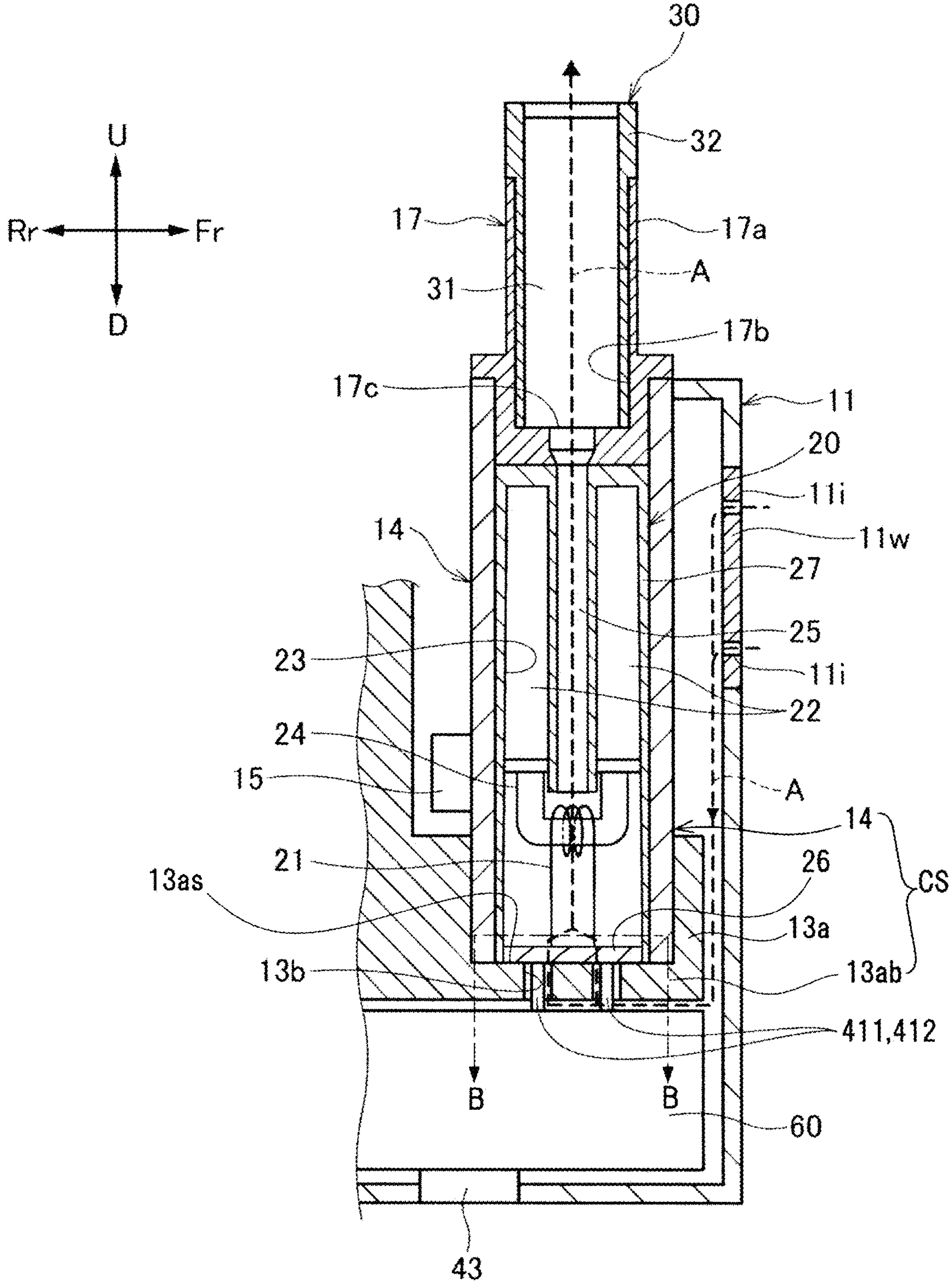
FIG. 3 is a schematic cross-sectional view of the aerosol inhaler in FIG. 1.
Figure 4:
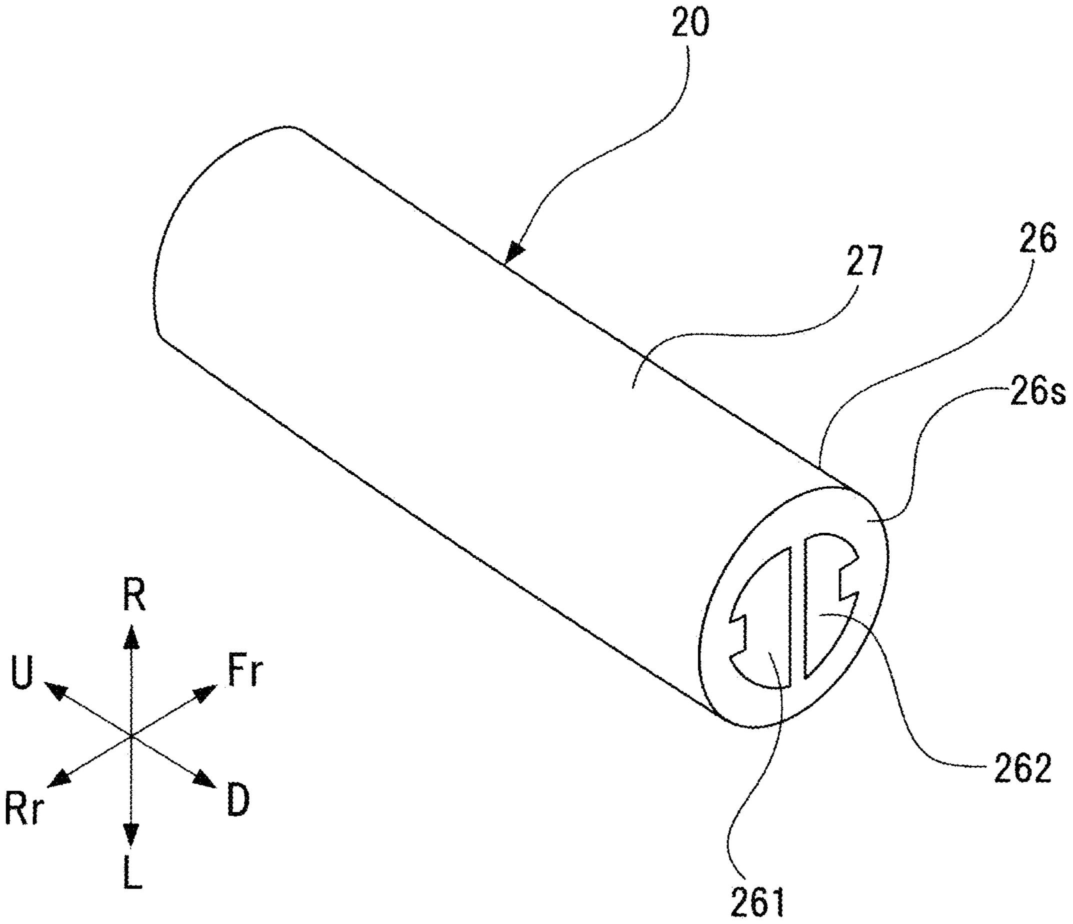
FIG. 4 is a perspective view of a first cartridge in the aerosol inhaler in FIG. 1.

As shown in FIGS. 1 to 3, the aerosol inhaler 1 includes a power supply unit 10, a first cartridge 20, and a second cartridge 30. The first cartridge 20 and the second cartridge 30 are attachable to and detachable from the power supply unit 10. In other words, the first cartridge 20 and the second cartridge 30 are replaceable. As shown in FIG. 4, the first cartridge 20 has a cylindrical outer shape. The outer shape of the first cartridge 20 may not be a complete cylindrical shape. For example, the shape may be a polygonal columnar shape of a regular polygon such as a regular hexadecagon, or a columnar shape with rounded corners.

(Power Supply Unit)

As shown in FIGS. 1 and 2, the power supply unit 10 accommodates, in a substantially rectangular parallelepiped power supply unit case 11 (hereinafter, also referred to as in the case), a power supply 12, an internal holder 13, a circuit board 60, and various sensors such as an intake sensor 15. The power supply 12, the circuit board 60 (including a micro controller unit (MCU) 50, an energization switching circuit 51, a resistance measurement circuit 52, a resistance measurement circuit 53, a resistance measurement circuit 54, a protruding electrode 411, a protruding electrode 412, a protruding electrode 413, a charging terminal 43, and the like, which will be described later), and the like are collectively accommodated in the power supply unit case 11 so as to be easily carried by a user and thus improve convenience for the user.

The power supply unit case 11 includes a first case 11A and a second case 11B that are attachable and detachable in the left-right direction (thickness direction). By assembling the first case 11A and the second case 11B in the left-right direction (thickness direction), a front surface, a rear surface, a left surface, a right surface, and a lower surface of the power supply unit 10 are formed. An upper surface of the power supply unit 10 is formed by a display 16.

A mouthpiece 17 is provided on the upper surface of the power supply unit 10 in front of the display 16. As shown in FIG. 3, an inhalation port 17*a* of the mouthpiece 17 protrudes further upward relative to the display 16.

An inclined surface that is inclined downward toward the rear side is provided between the upper surface and the rear surface of the power supply unit 10. An operation unit 18 that can be operated by the user is provided on the inclined surface. The operation unit 18 is implemented by a button-type switch, a touch panel, or the like. The operation unit 18 is used, for example, when the MCU 50 and the various sensors are activated or shut off as reflection of intention of use of the user.

The charging terminal 43 that is electrically connectable to an external power supply (not shown) that can charge the power supply 12 is provided on the lower surface of the power supply unit 10. The charging terminal 43 is, for example, a receptacle into which a mating plug (not shown) can be inserted. As the charging terminal 43, a receptacle into which various USB terminals (plugs) or the like can be inserted can be used. As an example, in the present embodiment, the charging terminal 43 is a USB Type-C receptacle. Accordingly, the power supply unit 10 (that is, the aerosol inhaler 1) is easily charged at various locations (places), and thus it possible to ensure (secure) an opportunity to charge the power supply unit 10.

In addition, the charging terminal 43 may include, for example, a power receiving coil, and may be configured to receive power transmitted from the external power supply in a non-contact manner. A method of wireless power transfer in this case may be an electromagnetic induction type, a magnetic resonance type, or a combination of the electromagnetic induction type and the magnetic resonance type. As another example, the charging terminal 43 may be connectable to various USB terminals, and may include the power receiving coil described above.

The internal holder 13 includes a rear wall 13*r* extending along the rear surface of the power supply unit 10, a central wall 13*c* that is provided at a front-rear direction central portion in the case and extends in parallel to the rear wall 13*r*, an upper wall 13*u* that extends along the display 16 and connects the rear wall 13*r* and the central wall 13*c*, a partition wall 13*d* that is orthogonal to the rear wall 13*r*, the central wall 13*c*, and the upper wall 13*u* and divides a space defined by the rear wall 13*r*, the central wall 13*c*, and the upper wall 13*u* into a left space and a right space, and a cartridge holding portion 13*a* that is connected to the central wall 13*c* and located in front of the central wall 13*c* above the lower surface of the power supply unit 10. As shown in FIGS. 2 and 3, the cartridge holding portion 13*a* is a cylindrical member with a bottom, which an opening in an upper end side and whose axial direction is along the up-down direction.

The power supply 12 is arranged in the left space of the internal holder 13. The power supply 12 is a rechargeable secondary battery, an electric double layer capacitor or the like, and is preferably a lithium ion secondary battery. An electrolyte of the power supply 12 may be formed of one or a combination of a gel-like electrolyte, an electrolytic solution, a solid electrolyte, and an ionic liquid.

The L-shaped circuit board 60 is arranged in a space formed by the right space of the internal holder 13 and a lower space formed between the cartridge holding portion 13*a* and the lower surface of the power supply unit 10. The circuit board 60 is formed by stacking a plurality of layers (four layers in the present embodiment) of boards, and is mounted with electronic components such as the MCU 50.

The MCU 50 is connected to various sensor devices such as the intake sensor 15 that detects a puff (intake) operation, the operation unit 18 and a notification unit 45. The MCU 50 is a control device (controller) that performs various types of control of the aerosol inhaler 1, including control of discharging to a load 21 (see FIG. 3) in order to heat the load 21 (so as to generate aerosol), which will be described later. Specifically, the MCU 50 is mainly implemented by a processor, and further includes storage media, such as a random access memory (RAM) necessary for operations of the processor and a read only memory (ROM) that stores various types of information. The processor in the present specification is, for example, an electric circuit in which circuit elements such as semiconductor elements are combined.

As shown in FIG. 3, a lower end portion of a cylindrical cartridge holder 14 that holds the first cartridge 20 is arranged on an inner peripheral portion of the cartridge holding portion 13*a*. A bottom wall portion 13*ab* of the cartridge holding portion 13*a* and the cartridge holder 14 constitute a cartridge accommodating portion CS with a bottom and cylindrical shape, which accommodates the first cartridge 20. The bottom wall portion 13*ab* constitutes a bottom portion of the cartridge accommodating portion CS. An upper surface of the bottom wall portion 13*ab* constitutes a bottom surface 13*as* of the cartridge accommodating portion CS.

An inner peripheral portion of the cartridge holder 14 has a shape corresponding to the outer shape of the first cartridge 20. Between an inner peripheral surface of the cartridge holder 14 and an outer peripheral surface of the first cartridge 20, a minute gap is formed to such an extent that the first cartridge 20 can slightly rotate in a circumferential direction due to an impact, vibration, or the like applied to the power supply unit 10.

The cartridge accommodating portion CS and the first cartridge 20 are not provided with any mechanism configured to position the first cartridge 20 in the circumferential direction (a direction around a center line of the first cartridge 20) in the cartridge accommodating portion CS. That is, in a state in which the first cartridge 20 is accommodated in the cartridge accommodating portion CS, when a force that rotates the first cartridge 20 in the circumferential direction is applied to the first cartridge 20, the first cartridge 20 can be rotated by 360 degrees.

The bottom wall portion 13*ab* of the cartridge holding portion 13*a* is provided with a through hole 13*b* that receives each of the protruding electrode 411, the protruding electrode 412, and the protruding electrode 413 (see FIGS. 3 and 5) that are provided so as to protrude from the circuit board 60 toward the first cartridge 20. The protruding electrode 411, the protruding electrode 412, and the protruding electrode 413 constitute a second electrode portion. Each of the protruding electrode 411, the protruding electrode 412, and the protruding electrode 413 is electrically connectable to the power supply 12, and is implemented by, for example, a pin in which a spring is provided. The through hole 13*b* provided corresponding to each of the protruding electrode 411, the protruding electrode 412, and the protruding electrode 413 is larger than the respective protruding electrodes, and is configured such that air flows into the first cartridge 20 through a gap formed between the through hole 13*b* and each protruding electrode.

As shown in FIG. 2, the intake sensor 15 that detects the puff operation is provided on an outer peripheral surface 14*a* of the cartridge holder 14 at a position facing the circuit board 60. The intake sensor 15 may be implemented by a condenser microphone, a pressure sensor, or the like. The cartridge holder 14 is provided with a hole portion 14*b* that is elongated in the up-down direction and through which a remaining amount of an aerosol source 22 stored in the first cartridge 20 can be visually observed. As shown in FIG. 1, in the power supply unit case 11, a remaining amount check window 11*w* having translucency is formed. The remaining amount of the aerosol source 22 stored in the first cartridge 20 can be visually observed from the remaining amount check window 11*w* through the hole portion 14*b* of the first cartridge 20. The remaining amount check window 11*w* is provided with an air inlet 11*i* through which outside air is taken into the case.

As shown in FIG. 3, the mouthpiece 17 is detachably fixed to an upper end portion of the cartridge holder 14. The second cartridge 30 is detachably fixed to the mouthpiece 17. The mouthpiece 17 includes a cartridge accommodating portion 17*b* that accommodates a part of the second cartridge 30, and a communication path 17*c* that allows the first cartridge 20 and the cartridge accommodating portion 17*b* to communicate with each other.

(First Cartridge)

As shown in FIG. 3, inside a cylindrical cartridge case 27, the first cartridge 20 includes a reservoir 23 that stores the aerosol source 22, the electrical load 21 that atomizes the aerosol source 22, a wick 24 that draws the aerosol source from the reservoir 23 to the load 21, and an aerosol flow path 25 through which aerosol generated by the atomization of the aerosol source 22 flows toward the second cartridge 30.

The reservoir 23 is partitioned to surround a periphery of the aerosol flow path 25, and stores the aerosol source 22. A porous body, such as a resin web or cotton, may be accommodated in the reservoir 23, and the porous body may be impregnated with the aerosol source 22. The reservoir 23 may only store the aerosol source 22 without accommodating the porous body such as the resin web or cotton. The aerosol source 22 contains a liquid such as glycerin, propylene glycol or water.

The wick 24 is a liquid holding member that draws the aerosol source 22 from the reservoir 23 to the load 21 by utilizing a capillary action. The wick 24 is made of, for example, glass fiber or porous ceramic.

The load 21 is a heating element (that is, a heater) that heats the aerosol source 22 without combustion, and is implemented by, for example, a heating wire (coil) wound to have a predetermined pitch. The load 21 heats the aerosol source 22 so as to atomize the aerosol source 22. As the load 21, a heating resistor, a ceramic heater, an induction heating type heater, or the like can be used. The load 21 may also be implemented by an element capable of atomizing the aerosol source 22 without heating, such as an ultrasonic element.

The aerosol flow path 25 is provided downstream of the load 21 on the center line of the first cartridge 20.

As shown in FIG. 4, a first electrode portion electrically connected to the load 21 and including a plate electrode 261 and a plate electrode 262 is provided on a lower end portion 26 of the cartridge case 27 of the first cartridge 20. The plate electrode 261 and the plate electrode 262 are exposed on a surface 26*s* of the lower end portion 26. One terminal of the load 21 in the first cartridge 20 is connected to the plate electrode 261, and the other terminal of the load 21 is connected to the plate electrode 262. The load 21 is supplied with power from the power supply 12 via two electrodes, that is, one electrode abutted against and electrically connected to the plate electrode 261 and one electrode abutted against and electrically connected to the plate electrode 262 among the protruding electrodes 411, 412, and 413 on the power supply unit 10 side, so as to atomize the aerosol source 22.

Figure 5:
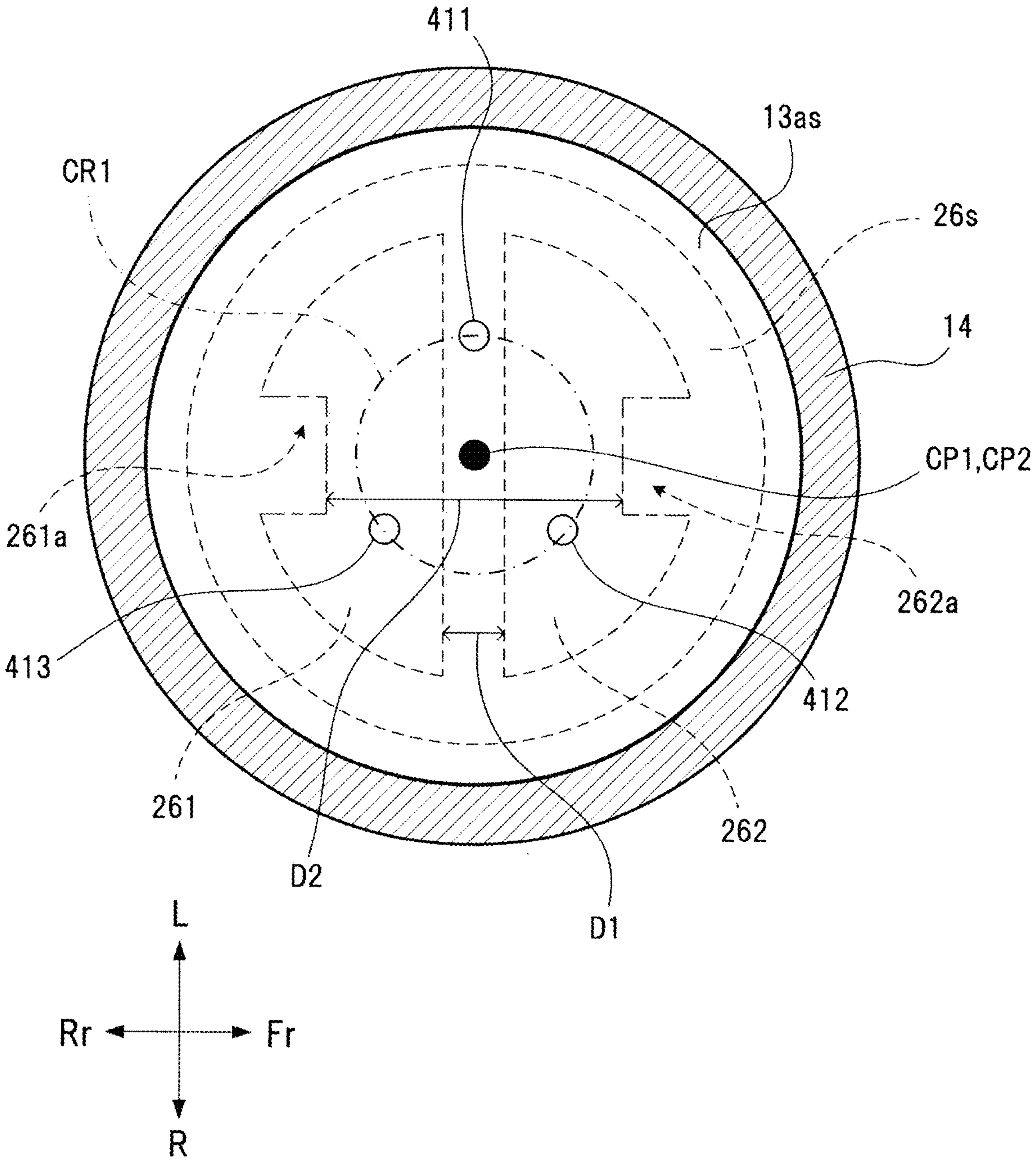
FIG. 5 is a schematic cross-sectional view taken along line B-B in FIG. 3.

FIG. 5 is a schematic cross-sectional view of the cartridge accommodating portion CS taken along line B-B shown in FIG. 3. In FIG. 5, the surface 26*s* (an end surface on the bottom wall portion 13*ab* side of the first cartridge 20) of the lower end portion 26 of the first cartridge 20 that is abutted against the bottom surface 13*as* of the cartridge accommodating portion CS is indicated by broken lines in the first cartridge 20. FIG. 5 shows a state in which a center CP1 (a position of a center line) of the first cartridge 20 and a center CP2 (a position of a center line) of the cartridge accommodating portion CS coincide with each other. A gap between an inner peripheral surface of the cartridge accommodating portion CS and the outer peripheral surface of the first cartridge 20 is minute, and in a state in which the first cartridge 20 is accommodated in the cartridge accommodating portion CS, as shown in FIG. 5, the center CP1 and the center CP2 substantially coincide with each other.

First, a configuration of the first electrode portion provided on the lower end portion 26 of the first cartridge 20 will be described with reference to FIG. 5. The plate electrode 261 provided in the first electrode portion has a substantially semicircular shape in which both ends of an arc are connected by a straight line, and includes a notch 261*a* at a center of the arc portion. The plate electrode 262 provided in the first electrode portion has a substantially semicircular shape in which both ends of an arc are connected by a straight line, and includes a notch 262*a* at a center of the arc portion. The plate electrode 261 and the plate electrode 262 are arranged to face each other with the center CP1 of the first cartridge 20 interposed therebetween such that the center CP1 overlaps a straight line connecting the notch 261*a* and the notch 262*a*. The plate electrode 261 and the plate electrode 262 have the same shape, and are arranged such that one of the plate electrode 261 and the plate electrode 262 overlaps the other when the one of the plate electrode 261 and the plate electrode 262 is rotated by 180 degrees about the center CP1. That is, the plate electrode 261 and the plate electrode 262 have a point-symmetric relationship with the center CP1 serving as a point of symmetry.

A configuration of the second electrode portion provided on the bottom wall portion 13*ab* of the cartridge accommodating portion CS will be described. FIG. 5 shows a virtual circle CR1 centered on the center CP2 of the cartridge accommodating portion CS. A diameter of the virtual circle CR1 is larger than a distance D1 between the plate electrode 261 and the plate electrode 262. In addition, the diameter of the virtual circle CR1 is smaller than a distance D2 between the notch 261*a* and the notch 262*a*. It should be noted that the notch 261*a* and the notch 262*a* are not necessary in the plate electrode 261 and the plate electrode 262, and can be omitted. In this case, the diameter of the virtual circle CR1 may be larger than the distance D1 and smaller than a length of a line segment connecting the center CP1 and one point on the arc of the plate electrode 261.

The protruding electrode 411, the protruding electrode 412, and the protruding electrode 413 provided in the second electrode portion are arranged on the virtual circle CR1 at equal intervals in a circumferential direction of the virtual circle CR1. That is, an angle formed by a line segment connecting the protruding electrode 411 and the center CP2 and a line segment connecting the protruding electrode 412 and the center CP2 is 120 degrees, an angle formed by the line segment connecting the protruding electrode 412 and the center CP2 and a line segment connecting the protruding electrode 413 and the center CP2 is 120 degrees, and an angle formed by the line segment connecting the protruding electrode 413 and the center CP2 and the line segment connecting the protruding electrode 411 and the center CP2 is 120 degrees. It should be noted that the protruding electrodes 411, 412, and 413 provided in the second electrode portion may not be arranged at equal intervals on the virtual circle CR1. The protruding electrode 411, the protruding electrode 412, and the protruding electrode 413 may be arranged such that at least one protruding electrode is abutted against the plate electrode 261 and at least one protruding electrode is abutted against the plate electrode 262 wherever the rotation position of the first cartridge 20 is located in the state in which the first cartridge 20 is accommodated in the cartridge accommodating portion CS.

Figure 6:
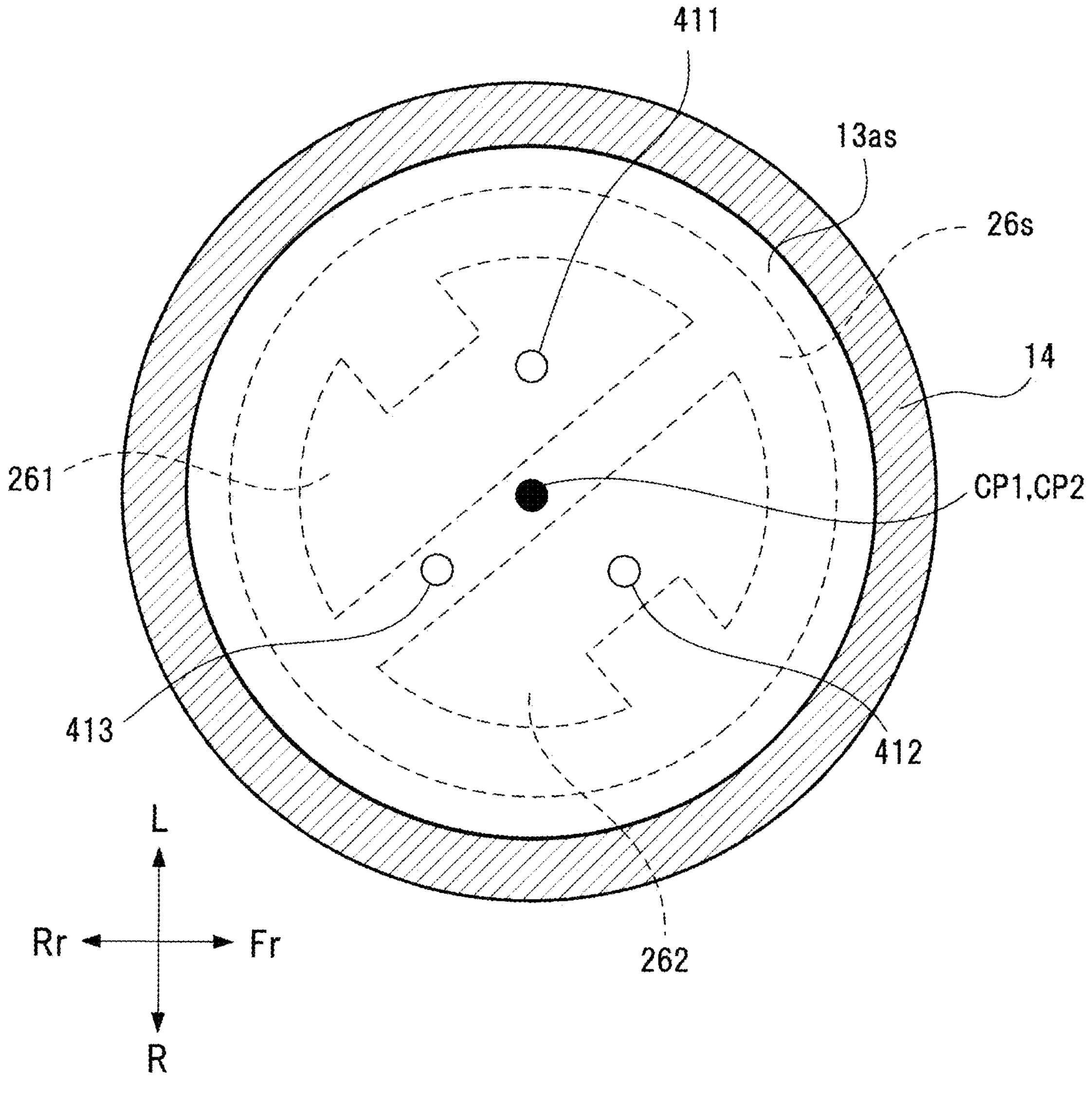
FIG. 6 is a schematic view showing a state in which the first cartridge rotates clockwise from the state in FIG. 5.
Figure 7:
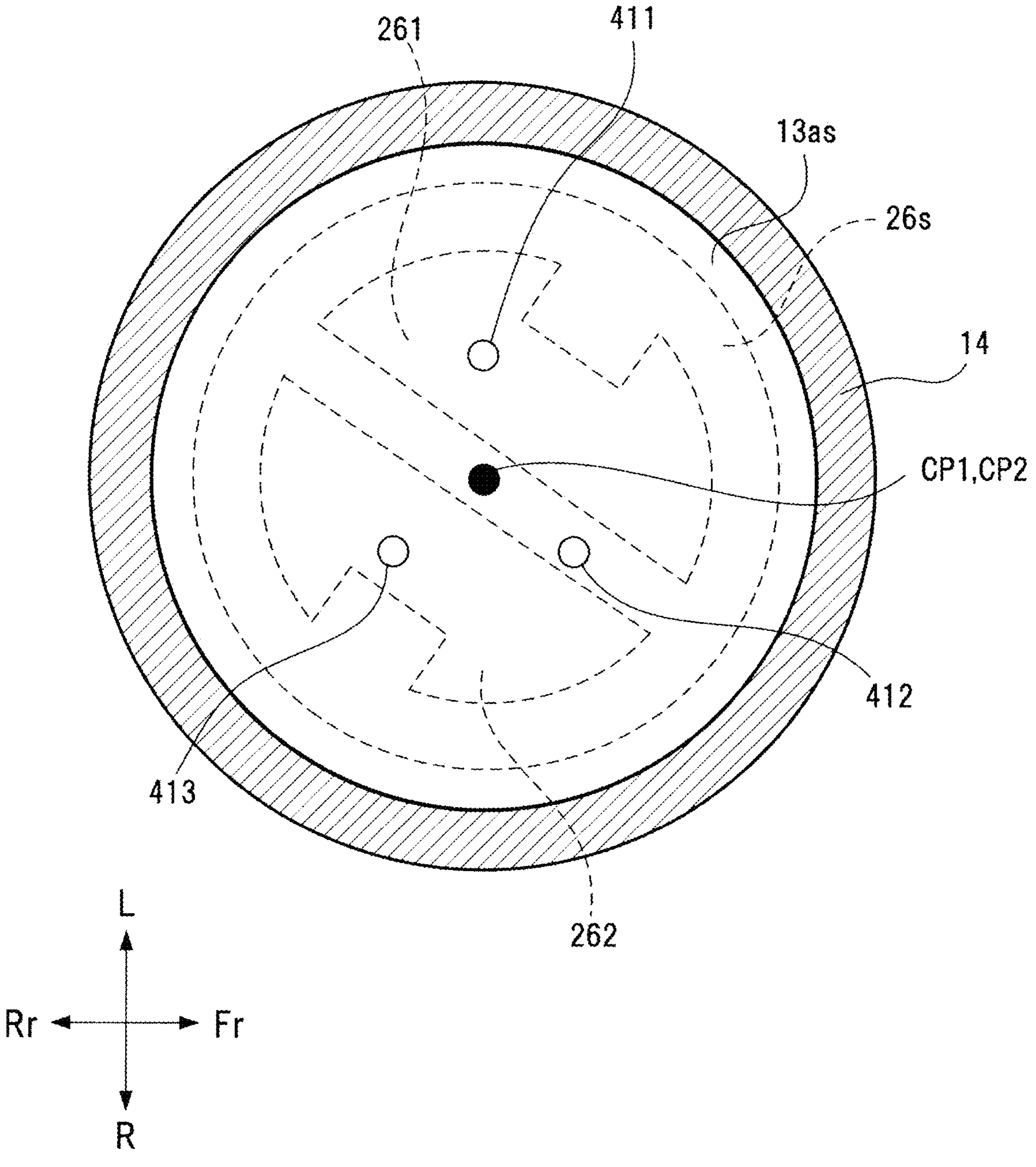
FIG. 7 is a schematic view showing a state in which the first cartridge rotates clockwise from the state in FIG. 6.
Figure 8:
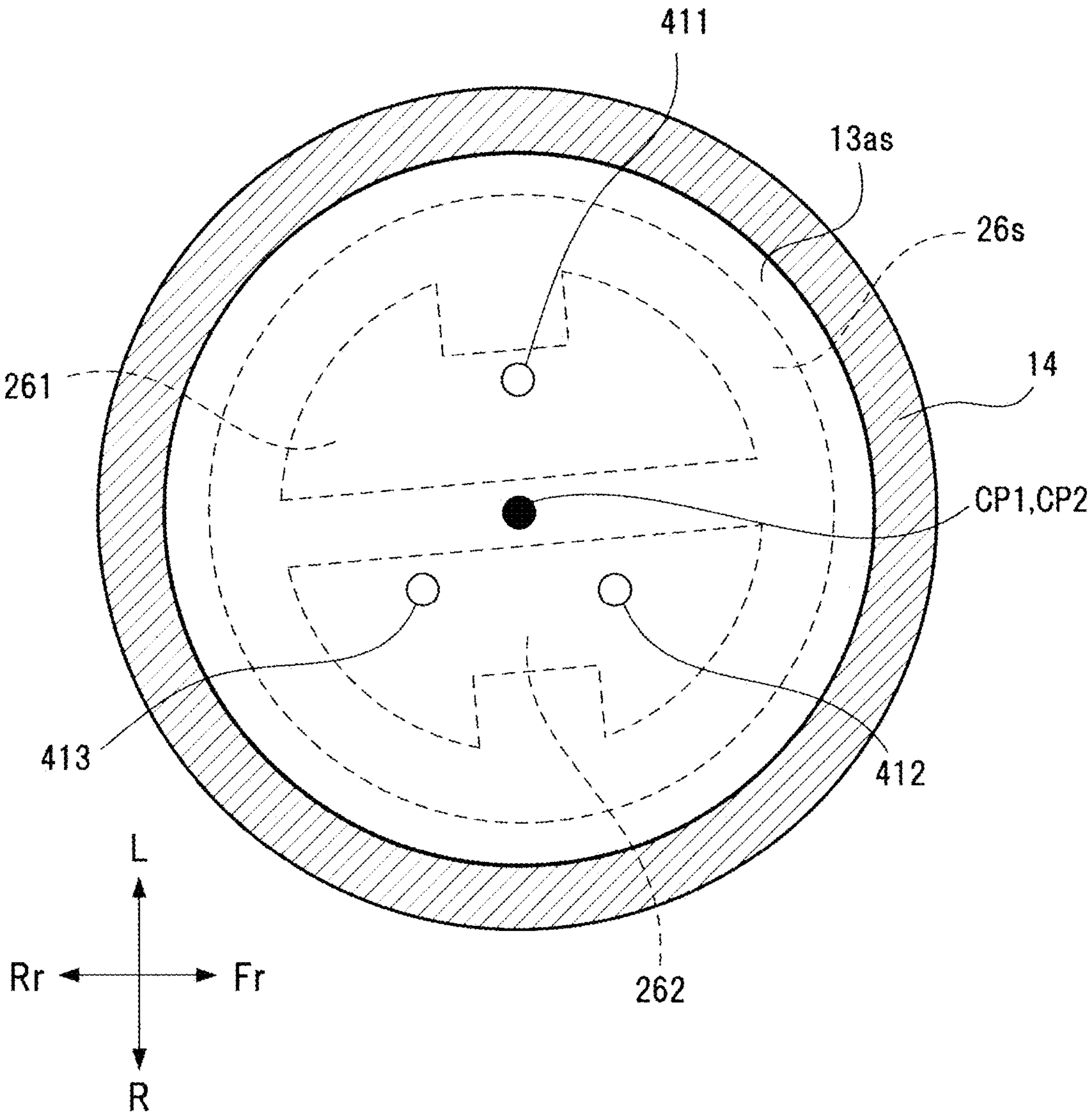
FIG. 8 is a schematic view showing a state in which the first cartridge rotates clockwise from the state in FIG. 6.

As described above, the first cartridge 20 is rotatable in the cartridge accommodating portion CS. That is, there is no limitation on an insertion posture of the first cartridge 20 inserted into the cartridge accommodating portion CS (the rotation position of the first cartridge 20 in the circumferential direction). Therefore, depending on how the first cartridge 20 is inserted into the cartridge accommodating portion CS, as shown in FIGS. 6 to 8, the first cartridge 20 may be accommodated in a state in which the first cartridge 20 rotates clockwise as compared with the state in FIG. 5.

In the present embodiment, the three protruding electrodes (the protruding electrode 411, the protruding electrode 412, and the protruding electrode 413), which are more than the total number (=2) of the plate electrodes provided in the first electrode portion, are provided in the cartridge accommodating portion CS with respect to the first electrode portion (the plate electrode 261 and the plate electrode 262) provided in the first cartridge 20. The protruding electrodes 411, 412, and 413 are arranged at equal intervals on the virtual circle CR1. Therefore, when the first cartridge 20 rotates 360 degrees about the center CP1, one or two of the protruding electrode 411, the protruding electrode 412, and the protruding electrode 413 are always in contact with each of the plate electrode 261 and the plate electrode 262. That is, in a state in which a gap between the plate electrode 261 and the plate electrode 262 overlaps one protruding electrode, as shown in FIGS. 5 to 7, one of the remaining two protruding electrodes is abutted against the plate electrode 261, and the other of the remaining two protruding electrodes is abutted against the plate electrode 262, so that the load 21 can be energized. As shown in FIG. 8, in a state in which the protruding electrodes do not overlap the gap, two protruding electrodes are abutted against one of the plate electrode 261 and the plate electrode 262, and one protruding electrode is abutted against the other of the plate electrode 261 and the plate electrode 262, so that the load 21 can be energized.

In this way, the second electrode portion provided on the cartridge accommodating portion CS is arranged such that at least one electrode of the second electrode portion is in contact with each electrode of the first electrode portion regardless of the rotation position of the first cartridge 20 in the cartridge accommodating portion CS.

(Second Cartridge)

The second cartridge 30 stores a fragrance source 31. The second cartridge 30 is detachably accommodated in the cartridge accommodating portion 17*b* provided in the mouthpiece 17.

The aerosol generated by atomizing the aerosol source 22 by the load 21 passes through the fragrance source 31 in the second cartridge 30, so that a fragrance is added to the aerosol. Chopped tobacco or a molded body obtained by molding a tobacco raw material into particles can be used as a raw material piece that implements the fragrance source 31. The fragrance source 31 may also be implemented by a plant other than tobacco (for example, mint, Chinese herb, or herb). A flavor additive such as menthol may also be added to the fragrance source 31.

The aerosol inhaler 1 can generate the aerosol to which the fragrance is added by the aerosol source 22, the fragrance source 31, and the load 21. That is, the aerosol source 22 and the fragrance source 31 constitute an aerosol generation source that generates the aerosol to which the fragrance is added.

In addition to a configuration in which the aerosol source 22 and the fragrance source 31 are separated from each other, a configuration in which the fragrance source 31 is omitted and substances that can be contained in the fragrance source 31 are added to the aerosol source 22, or a configuration in which a medicine or the like is added to the aerosol source 22 instead of the fragrance source 31 may also be adopted as the configuration of the aerosol generation source used in the aerosol inhaler 1.

In the aerosol inhaler 1 configured as described above, when the user inhales, the intake sensor 15 detects the puff operation and inputs an aerosol generation request to the MCU 50. The MCU 50 that receives the aerosol generation request performs control of discharging from the power supply 12 to the load 21 so as to generate the aerosol. As shown by arrow A in FIG. 3, air flowing in from the air inlet 11*i* provided in the power supply unit case 11 due to the inhalation of the user flows into the cartridge accommodating portion CS through the gap formed between the through hole 13*b* and the protruding electrodes 411, 412, 413. The air flows into the first cartridge 20 from a minute hole (not shown) formed in the lower end portion 26 of the first cartridge 20, and passes through the vicinity of the load 21. The load 21 atomizes the aerosol source 22 drawn by the wick 24 from the reservoir 23. The aerosol generated by atomization flows through the aerosol flow path 25 together with the air flowing in from the minute hole, and is supplied to the second cartridge 30 via the communication path 17*c*. The aerosol supplied to the second cartridge 30 passes through the fragrance source 31 so as to put on the fragrance, and is then supplied to an inhalation port 32.

The aerosol inhaler 1 is provided with the notification unit 45 that notifies various types of information (see FIG. 2). The notification unit 45 may be implemented by a light emitting element, a vibration element, or a sound output element. The notification unit 45 may also be a combination of two or more of the light emitting element, the vibration element, and the sound output element. The notification unit 45 may be provided in any one of the power supply unit 10, the first cartridge 20, and the second cartridge 30, and is preferably provided in the power supply unit 10, which is not a consumable item.

In the present embodiment, an organic light emitting diode (OLED) panel 46 and a vibrator 47 are provided as the notification unit 45. An OLED of the OLED panel 46 emits light so as to notify the user of various types of information related to the aerosol inhaler 1 via the display 16. In addition, the vibrator 47 vibrates so as to notify the user of the various types of information related to the aerosol inhaler 1 via the power supply unit case 11. The notification unit 45 may be provided with only one of the OLED panel 46 and the vibrator 47, or may be provided with another light emitting element or the like. In addition, the information notified of by the OLED panel 46 and the information notified of by the vibrator 47 may be different or the same.

(Configuration of Electric Circuit Formed on Circuit Board)

Figure 9:
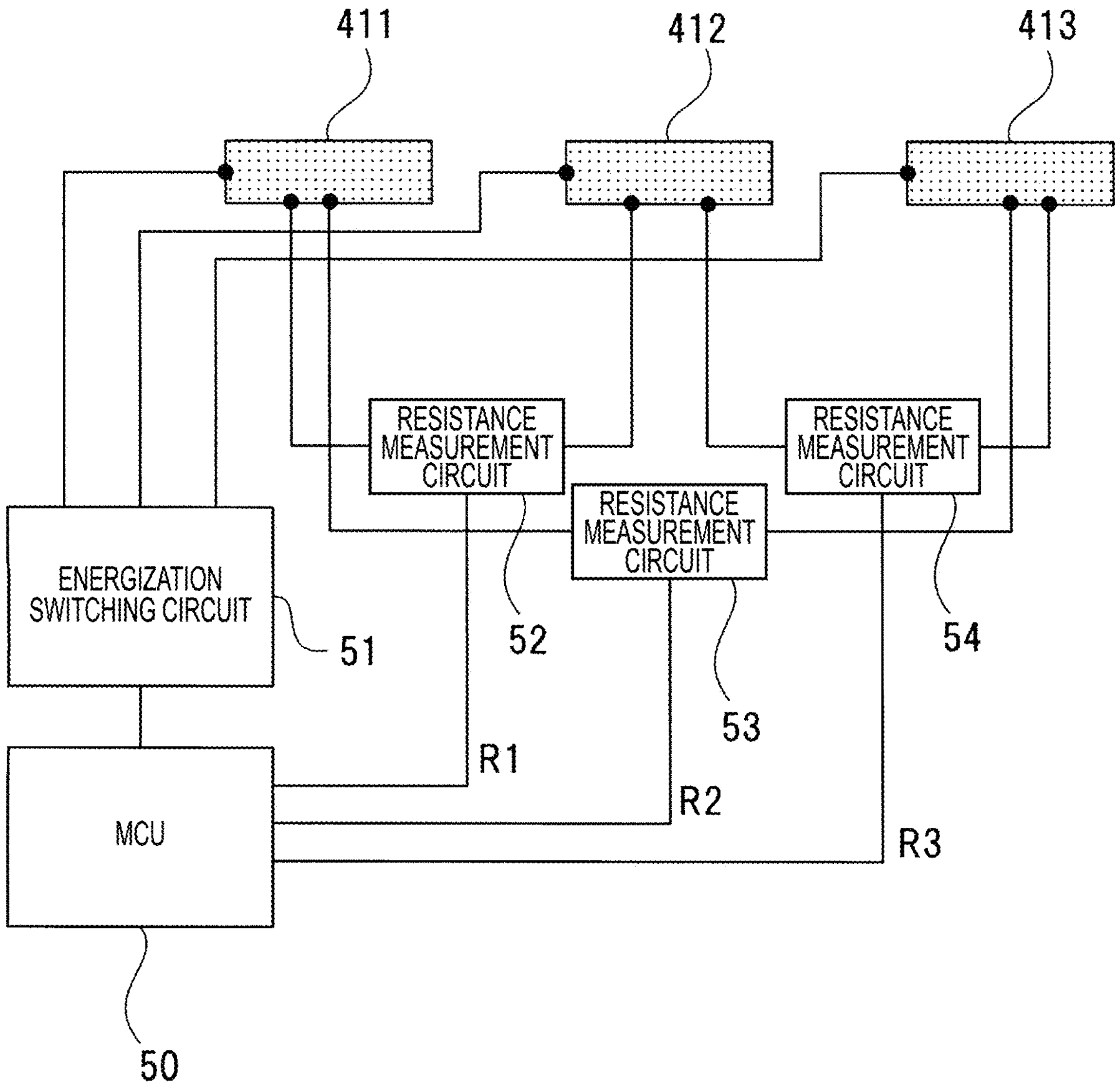
FIG. 9 is a schematic view of a circuit mounted on a circuit board of the aerosol inhaler in FIG. 2.

FIG. 9 is a schematic view showing a configuration of an electric circuit formed on the circuit board 60. The circuit board 60 is provided with the resistance measurement circuit 52, the resistance measurement circuit 53, the resistance measurement circuit 54, the energization switching circuit 51, and the MCU 50.

The resistance measurement circuit 52 is connected to the protruding electrode 411 and the protruding electrode 412, and transmits information corresponding to an electrical resistance value R1 between the protruding electrode 411 and the protruding electrode 412 to the MCU 50. For example, the resistance measurement circuit 52 causes a minute current to flow to the protruding electrode 411 and the protruding electrode 412, measures a voltage between the protruding electrode 411 and the protruding electrode 412 in this state, and transmits the voltage to the MCU 50 as the information corresponding to the electrical resistance value R1. The MCU 50 acquires the electrical resistance value R1 based on the voltage.

The resistance measurement circuit 53 is connected to the protruding electrode 411 and the protruding electrode 413, and transmits information corresponding to an electrical resistance value R2 between the protruding electrode 411 and the protruding electrode 413 to the MCU 50. For example, the resistance measurement circuit 53 causes a minute current to flow to the protruding electrode 411 and the protruding electrode 413, measures a voltage between the protruding electrode 411 and the protruding electrode 413 in this state, and transmits the voltage to the MCU 50 as the information corresponding to the electrical resistance value R2. The MCU 50 acquires the electrical resistance value R2 based on the voltage.

The resistance measurement circuit 54 is connected to the protruding electrode 412 and the protruding electrode 413, and transmits information corresponding to an electrical resistance value R3 between the protruding electrode 412 and the protruding electrode 413 to the MCU 50. For example, the resistance measurement circuit 54 causes a minute current to flow to the protruding electrode 412 and the protruding electrode 413, measures a voltage between the protruding electrode 412 and the protruding electrode 413 in this state, and transmits the voltage to the MCU 50 as the information corresponding to the electrical resistance value R3. The MCU 50 acquires the electrical resistance value R3 based on the voltage. As described above, the MCU 50 functions as a resistance measurement unit that acquires the electrical resistance values R1, R2, and R3 based on the information from the resistance measurement circuits 52, 53, and 54.

In the state in FIG. 5, the electrical resistance values R1 and R2 cannot be measured, and the electrical resistance value R3 is a value close to an electrical resistance value of the load 21. In the state in FIG. 6, the electrical resistance values R2 and R3 cannot be measured, and the electrical resistance value R1 is a value close to the electrical resistance value of the load 21. In the state in FIG. 7, the electrical resistance values R1 and R3 cannot be measured, and the electrical resistance value R2 is a value close to the electrical resistance value of the load 21. In the state in FIG. 8, the electrical resistance value R3 is a minute value, and the electrical resistance values R1 and R2 are values close to the electrical resistance value of the load 21.

The energization switching circuit 51 includes a switch and the like, and switches among a state in which power supplied from the power supply 12 is supplied to an electrode pair of the protruding electrode 411 and the protruding electrode 412, a state in which the power is supplied to an electrode pair of the protruding electrode 412 and the protruding electrode 413, and a state in which the power is supplied to an electrode pair of the protruding electrode 411 and the protruding electrode 413.

The MCU 50 determines an electrode pair to which the power (including at least power for atomizing the aerosol source 22) from the power supply 12 is to be supplied based on the electrical resistance values R1, R2, and R3, and controls the energization switching circuit 51 such that the power is supplied to the determined electrode pair.

Specifically, the MCU 50 selects an electrode pair in which the electrical resistance value between the electrodes is equal to or larger than a threshold value based on the electrical resistance values R1, R2, and R3. In the state in FIG. 5, the electrode pair of the protruding electrode 412 and the protruding electrode 413 is selected. In the state in FIG. 6, the electrode pair of the protruding electrode 411 and the protruding electrode 412 is selected. In the state in FIG. 7, the electrode pair of the protruding electrode 411 and the protruding electrode 413 is selected. In the state in FIG. 8, one of the electrode pair of the protruding electrode 411 and the protruding electrode 412 and the electrode pair of the protruding electrode 411 and the protruding electrode 413 is selected. In a case where there are a plurality of electrode pairs in which the electrical resistance value between the electrodes is equal to or larger than the threshold value, which electrode pair is preferentially selected may be determined in advance. Alternatively, energization record information may be stored for each protruding electrode, and an electrode pair including a protruding electrode having a smallest number of times of energization may be selected. Alternatively, another threshold value higher than the threshold value may be set, and an electrode pair having an electrical resistance value lower than the other threshold value may be selected from the plurality of electrode pairs having the electrical resistance value equal to or larger than the threshold value. Alternatively, a target value of the electrical resistance value may be set, and an electrode pair having an electrical resistance value between the electrodes closest to the target value may be selected.

Effects of Embodiment

In the aerosol inhaler 1, there is no positioning mechanism configured to position the first cartridge 20 in the cartridge accommodating portion CS in the circumferential direction. Therefore, the first cartridge 20 can be inserted into the cartridge accommodating portion CS without the user being conscious of a rotation posture of the first cartridge 20. Therefore, operability of installing the first cartridge 20 to the power supply unit 10 can be improved.

In addition, in the aerosol inhaler 1, the power supply unit 10 is provided with the second electrode portion including more electrodes than the first electrode portion. Therefore, the first cartridge 20 and the power supply unit 10 can be electrically connected to each other regardless of the rotation posture of the first cartridge 20, and thus the aerosol can be generated in the same manner as in the related art.

In addition, in the aerosol inhaler 1, the electrode pair to be energized in order to generate the aerosol is selected based on the electrical resistance values between the protruding electrodes of the second electrode portion. For example, in any one of the states in FIGS. 5 to 7, the protruding electrodes in contact with the plate electrodes 261 and 262 can be selected, and thus the aerosol can be generated by energizing the protruding electrodes. In addition, in the state in FIG. 8, the electrode pair of the protruding electrodes 412 and 413 in contact with the plate electrode 262 is short-circuited, whereas the electrode pair is not energized. In this way, it is possible to prevent a large amount of power necessary for generating the aerosol from being supplied to the electrode pair in the short-circuited state, and safety can thus be improved. As described above, even though the number of electrodes provided in the second electrode portion is three, two appropriate electrodes are selected therefrom and energized. Therefore, the aerosol can be generated safely in the same manner as in the related art without any positioning mechanism.

A timing when the MCU 50 acquires the electrical resistance values R1, R2, and R3 is preferably a period from a time point when a power supply of the aerosol inhaler 1 is turned on by an operation on the operation unit 18 to when an initial aerosol generation request is received (in other words, a period during which the aerosol source 22 is not atomized). In this way, the electrical resistance values R1, R2, and R3 can be measured before the large power for generating the aerosol is supplied to the first cartridge 20, and the electrode pair to be energized in the second electrode portion can be determined. Therefore, the aerosol can be safely generated.

(First Modification of Cartridge Accommodating Portion)

Figure 10:
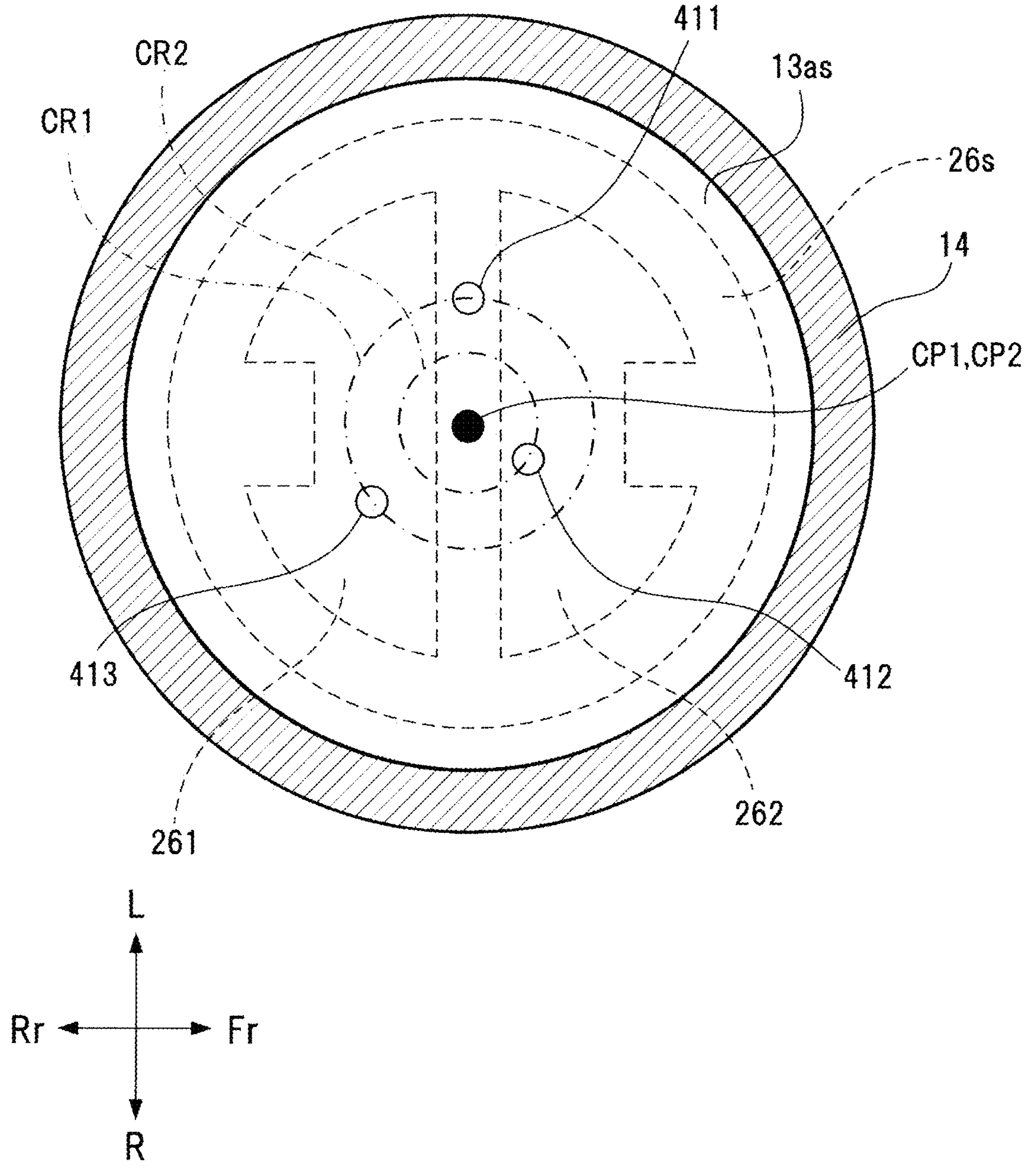
FIG. 10 is a schematic view showing a first modification of a cartridge accommodating portion in FIG. 3.

FIG. 10 is a schematic view showing a first modification of the cartridge accommodating portion CS, and is a schematic cross-sectional view corresponding to FIG. 5. A configuration in FIG. 10 is the same as the configuration in FIG. 5 except that a position of the protruding electrode 412 provided on the bottom wall portion 13*ab* of the cartridge accommodating portion CS is different.

FIG. 10 shows a virtual circle CR2 centered on the center CP2 of the cartridge accommodating portion CS. The virtual circle CR2 has a diameter smaller than that of the virtual circle CR1, and is located inside the virtual circle CR2. The diameter of the virtual circle CR2 is larger than the distance D1 described above. The protruding electrode 412 is arranged on the virtual circle CR2.

In the configuration in FIG. 10, the angle formed by the line segment connecting the protruding electrode 411 and the center CP2 and the line segment connecting the protruding electrode 412 and the center CP2 is 120 degrees, the angle formed by the line segment connecting the protruding electrode 412 and the center CP2 and the line segment connecting the protruding electrode 413 and the center CP2 is 120 degrees, and the angle formed by the line segment connecting the protruding electrode 413 and the center CP2 and the line segment connecting the protruding electrode 411 and the center CP2 is 120 degrees.

With the configuration as shown in FIG. 10, the same effects as those of the configuration in FIG. 5 can still be obtained. In addition, according to the configuration in FIG. 10, the cartridge accommodating portion CS can be compatible with the first cartridge 20 of a type in which a structure of the first electrode portion is different.

For example, a case is assumed in which the first cartridge 20 of another type including an annular-shaped first annular electrode overlapping with a circumferential edge of the virtual circle CR1 and an annular-shaped second annular electrode overlapping with a circumferential edge of the virtual circle CR2 as the first electrode portion is accommodated in the cartridge accommodating portion CS in a usable manner.

According to the configuration in FIG. 10, regardless of a rotation posture of the first cartridge 20 of the other type, the protruding electrodes 411 and 413 can always be in contact with the first annular electrode, and the protruding electrode 412 can always be in contact with the second annular electrode. In a state in which the protruding electrodes 411 and 413 are in contact with the first annular electrode and the protruding electrode 412 is in contact with the second annular electrode, the electrical resistance value between the protruding electrodes 411 and 412 and the electrical resistance value between the protruding electrodes 412 and 413 are both equal to or larger than the threshold value, and the electrical resistance value between the protruding electrodes 411 and 413 is less than the threshold value. Therefore, the MCU 50 controls the electrode to be supplied from the power supply 12 to the electrode pair of the protruding electrode 412 and the protruding electrode 411, or the electrode pair of the protruding electrode 412 and the protruding electrode 413, so that the first cartridge 20 of the other type can be energized so as to generate the aerosol. In this way, according to the configuration in FIG. 10, it is possible to implement the aerosol inhaler 1 compatible with the first cartridges 20 of various types, and thus a commercial value of the aerosol inhaler 1 can be improved.

In the configuration in FIG. 10, by arranging the protruding electrode 411 and the protruding electrode 413 in point symmetry with respect to the center CP2, it is possible to identify which one of the first cartridge 20 of the type shown in FIG. 4 and the first cartridge 20 of the other type is installed. Specifically, the MCU 50 firstly acquires a first electrical resistance value between the protruding electrodes 411 and 413, and, when the first electrical resistance value is equal to or larger than a threshold value, the MCU 50 recognizes that the first cartridge 20 of the type shown in FIG. 4 is installed. When the first electrical resistance value is less than the threshold value, the MCU 50 acquires a second electrical resistance value between the protruding electrodes 411 and 412 or the second electrical resistance value between the protruding electrodes 413 and 412, and, when the second electrical resistance value is equal to or larger than the threshold value, the MCU 50 recognizes that the first cartridge 20 of the other type is installed. When the second electrical resistance value is less than the threshold value, the MCU 50 determines that a connection error occurs, and notifies the user of the connection error. The MCU 50 may also notify the user of the recognized cartridge type. In addition, the MCU 50 may change the control of discharging to the first cartridge 20 according to the cartridge type. In this way, different types of cartridges can be used, optimal control can be performed according to the cartridge type, so that the commercial value of the aerosol inhaler 1 can be improved.

(Second Modification of Cartridge Accommodating Portion)

Figure 11:
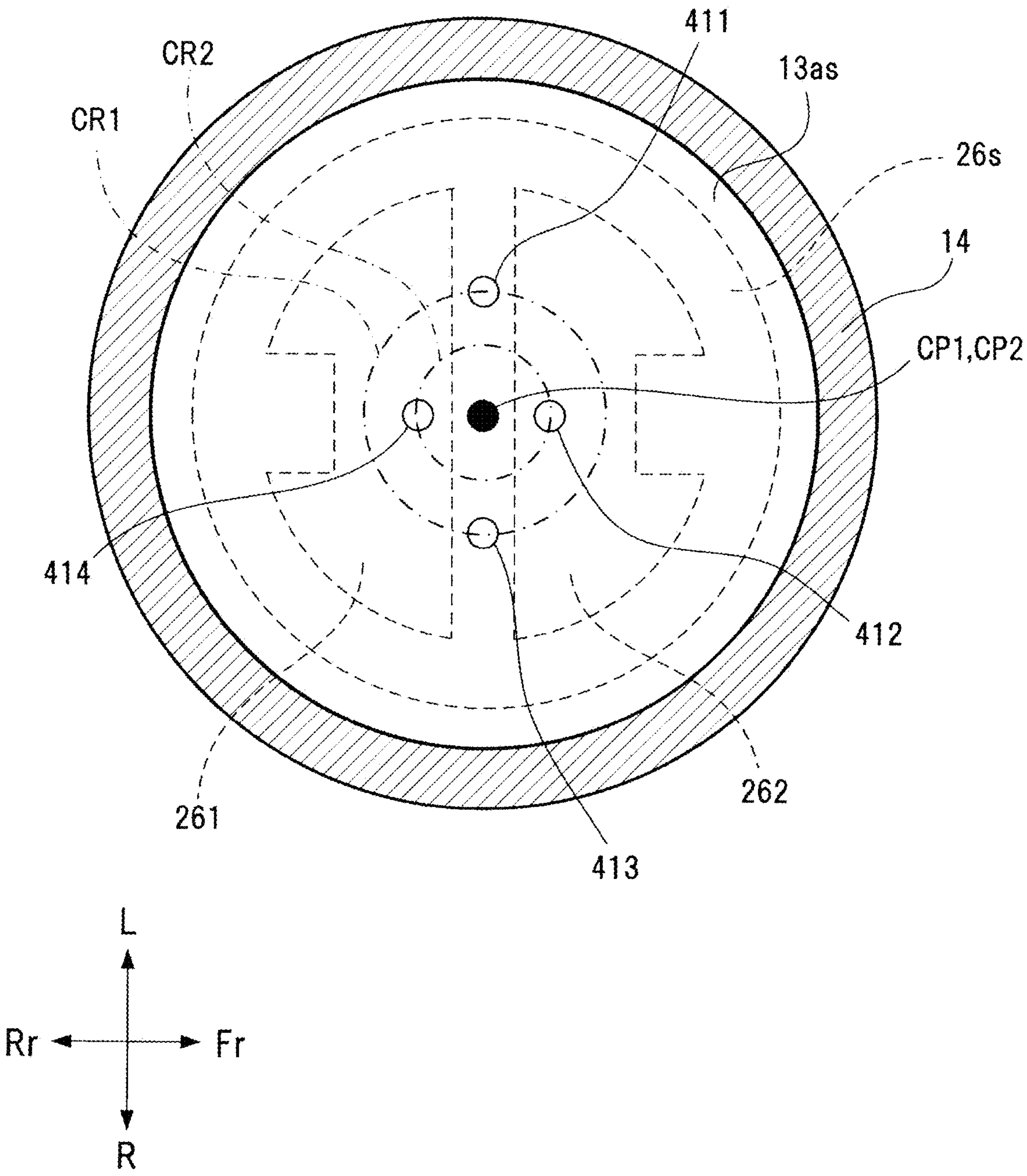
FIG. 11 is a schematic view showing a second modification of the cartridge accommodating portion in FIG. 3.

FIG. 11 is a schematic view showing a second modification of the cartridge accommodating portion CS, and is a schematic cross-sectional view corresponding to FIG. 5. A configuration in FIG. 11 is the same as the configuration in FIG. 5 except that positions of the protruding electrodes 411, 412, and 413 provided on the bottom wall portion 13*ab* of the cartridge accommodating portion CS are different, and a protruding electrode 414 is additionally provided on the bottom wall portion 13*ab*. The virtual circle CR2 shown in FIG. 11 is the same as the virtual circle CR2 shown in FIG. 10.

In the configuration in FIG. 11, the protruding electrodes 411 and 413 are arranged at equal intervals on the virtual circle CR1, and the protruding electrodes 412 and 414 are arranged at equal intervals on the virtual circle CR2. In the configuration in FIG. 11, an angle formed by two line segments connecting each of the protruding electrodes 411 and 412 and the center CP2, an angle formed by two line segments connecting each of the protruding electrodes 412 and 413 and the center CP2, an angle formed by two line segments connecting each of the protruding electrodes 413 and 414 and the center CP2, and an angle formed by two line segments connecting each of the protruding electrodes 414 and 411 and the center CP2 are each 90 degrees.

In a case where the configuration in FIG. 11 is adopted, the MCU 50 acquires an electrical resistance value between the electrodes of an electrode pair of the protruding electrode 411 and the protruding electrode 412, an electrical resistance value between the electrodes of an electrode pair of the protruding electrode 411 and the protruding electrode 413, an electrical resistance value between the electrodes of an electrode pair of the protruding electrode 411 and the protruding electrode 414, an electrical resistance value between the electrodes of an electrode pair of the protruding electrode 412 and the protruding electrode 413, an electrical resistance value between the electrodes of an electrode pair of the protruding electrode 412 and the protruding electrode 414, and an electrical resistance value between the electrodes of an electrode pair of the protruding electrode 413 and the protruding electrode 414. Then, the MCU 50 selects one electrode pair in which the acquired electrical resistance value is equal to or larger than a threshold value, and performs control to supply power from the power supply 12 to the selected electrode pair.

With the configuration as shown in FIG. 11, the same effects as those of the configurations in FIG. 5 and FIG. 10 can still be obtained. In addition, in the configuration in FIG. 11, the number of protruding electrodes provided in the second electrode portion is larger than in the configurations of FIG. 5 and FIG. 10. Therefore, a plurality of electrode pairs having an electrical resistance value equal to or larger than the threshold value can be provided with a high probability. Therefore, for example, it is easy to select an electrode pair such that each protruding electrode is used evenly for energization, and thus durability of the second electrode portion can be improved. In addition, according to the configuration in FIG. 11, since the protruding electrode 411 and the protruding electrode 413 are arranged in point symmetry with respect to the center CP2, and the protruding electrode 412 and the protruding electrode 414 are arranged in point symmetry with respect to the center CP2, the first cartridge 20 of the type shown in FIG. 4 and the first cartridge 20 of the other type described above can be identified, and thus the commercial value can be improved.

In the configuration in FIG. 11, the protruding electrodes 411, 412, 413, and 414 may also be arranged at equal intervals on either the virtual circle CR1 or the virtual circle CR2.

(Third Modification of Cartridge Accommodating Portion)

Figure 12:
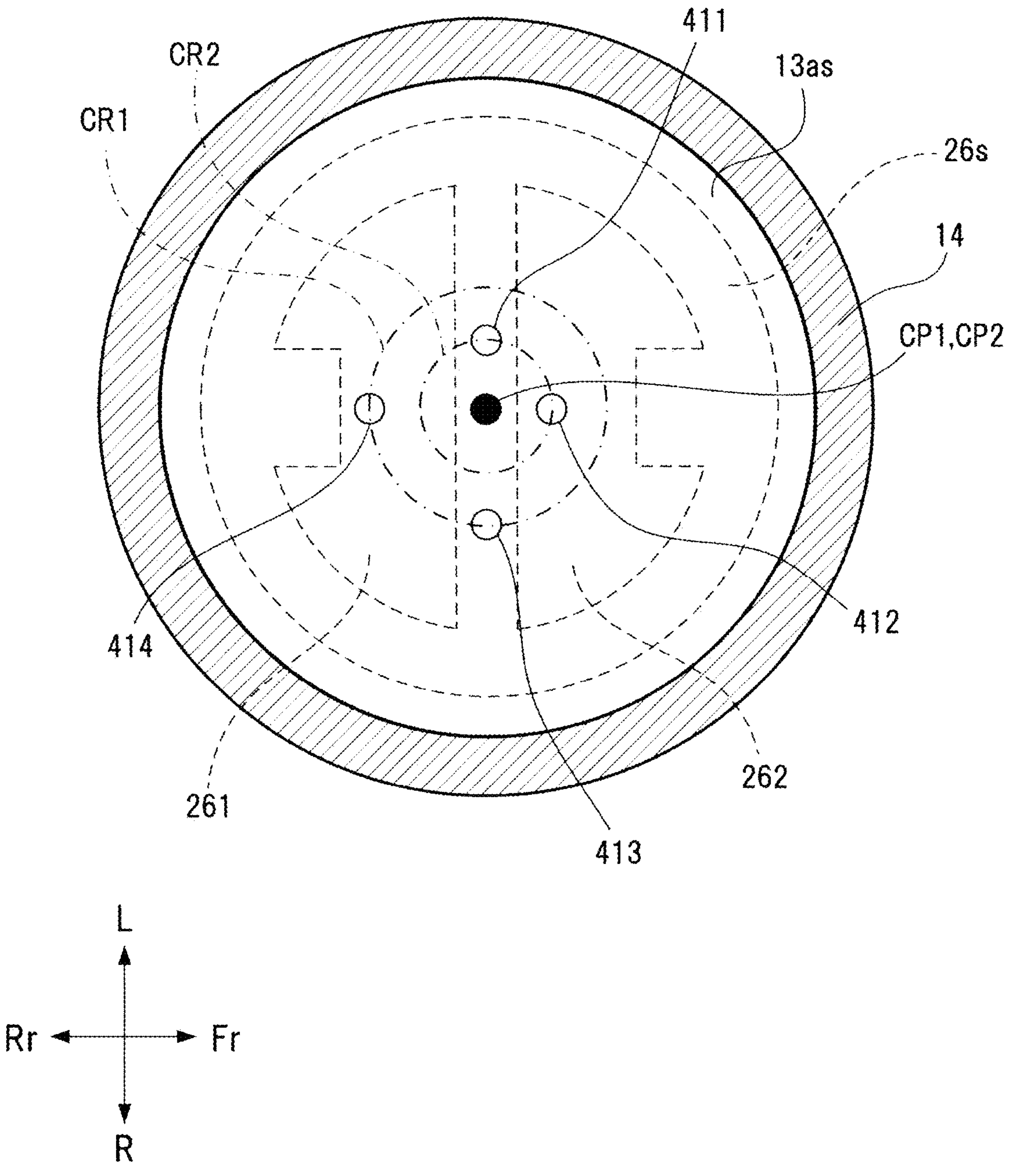
FIG. 12 is a schematic view showing a third modification of the cartridge accommodating portion in FIG. 3.

FIG. 12 is a schematic view showing a third modification of the cartridge accommodating portion CS, and is a schematic cross-sectional view corresponding to FIG. 5. A configuration in FIG. 12 is the same as the configuration in FIG. 11 except that positions of the protruding electrodes 411 and 414 are changed.

In the configuration in FIG. 12, the protruding electrode 411 is arranged on the virtual circle CR2, and the protruding electrode 414 is arranged on the virtual circle CR1. In the configuration in FIG. 12, the angle formed by the two line segments connecting each of the protruding electrodes 411 and 412 and the center CP2, the angle formed by the two line segments connecting each of the protruding electrodes 412 and 413 and the center CP2, the angle formed by the two line segments connecting each of the protruding electrodes 413 and 414 and the center CP2, and the angle formed by the two line segments connecting each of the protruding electrodes 414 and 411 and the center CP2 are each 90 degrees.

With the configuration as shown in FIG. 12, the same effects as those of the configuration in FIG. 11 can still be obtained.

In the configuration in FIG. 10 described above, the position of the protruding electrode 412 may be changed to the center CP2. In addition, in the configurations in FIGS. 11 and 12, the position of the protruding electrode 412 or the protruding electrode 414 may be changed to the center CP2. It is assumed that the first cartridge 20 is a second other type having a first electrode portion in which a circular electrode is arranged at the center CP1 and an annular electrode is arranged on the virtual circle CR1. According to the configuration in which the position of the protruding electrode 412 is changed to the center CP2 in the configuration in FIG. 10 or the configuration in which the position of the protruding electrode 412 or the protruding electrode 414 is changed to the center CP2 in the configuration in FIG. 11 or 12, by selecting an electrode pair to be energized based on the electrical resistance value between the electrode pairs, it is possible to be compatible with both the first cartridge 20 of the type shown in FIG. 4 and the first cartridge 20 of the second other type. In addition, it is possible to identify the type based on the electrical resistance values between the electrode pairs.

(Fourth Modification of Cartridge Accommodating Portion)

Figure 13:
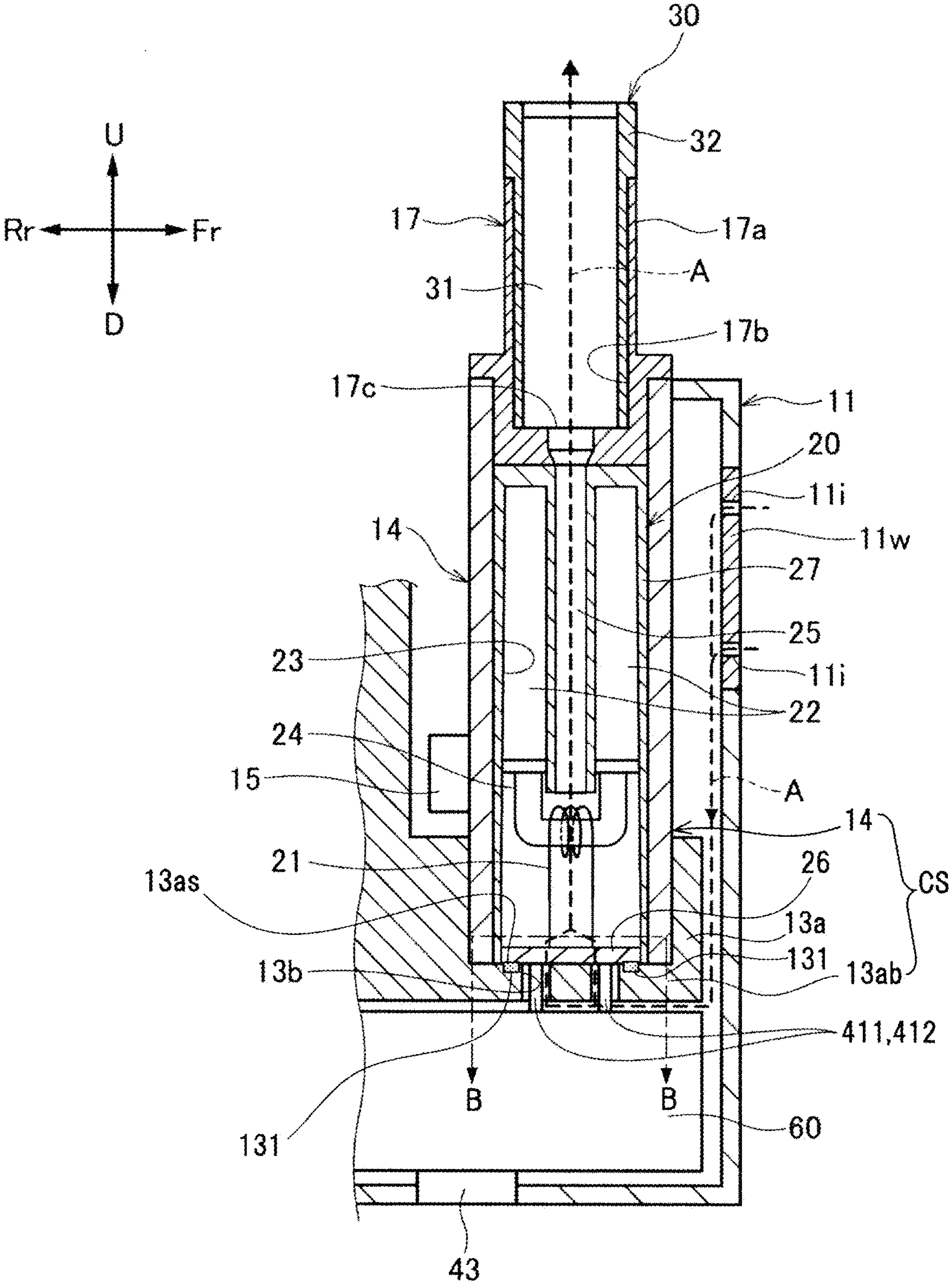
FIG. 13 is a schematic cross-sectional view showing a fourth modification of the cartridge accommodating portion in FIG. 3.

FIG. 13 is a view showing a fourth modification of the cartridge accommodating portion CS, and is a schematic cross-sectional view corresponding to FIG. 3. A configuration in FIG. 13 is the same as the configuration in FIG. 3 except that an annular member 131 is provided on the bottom wall portion **13*ab***.

Figure 14:
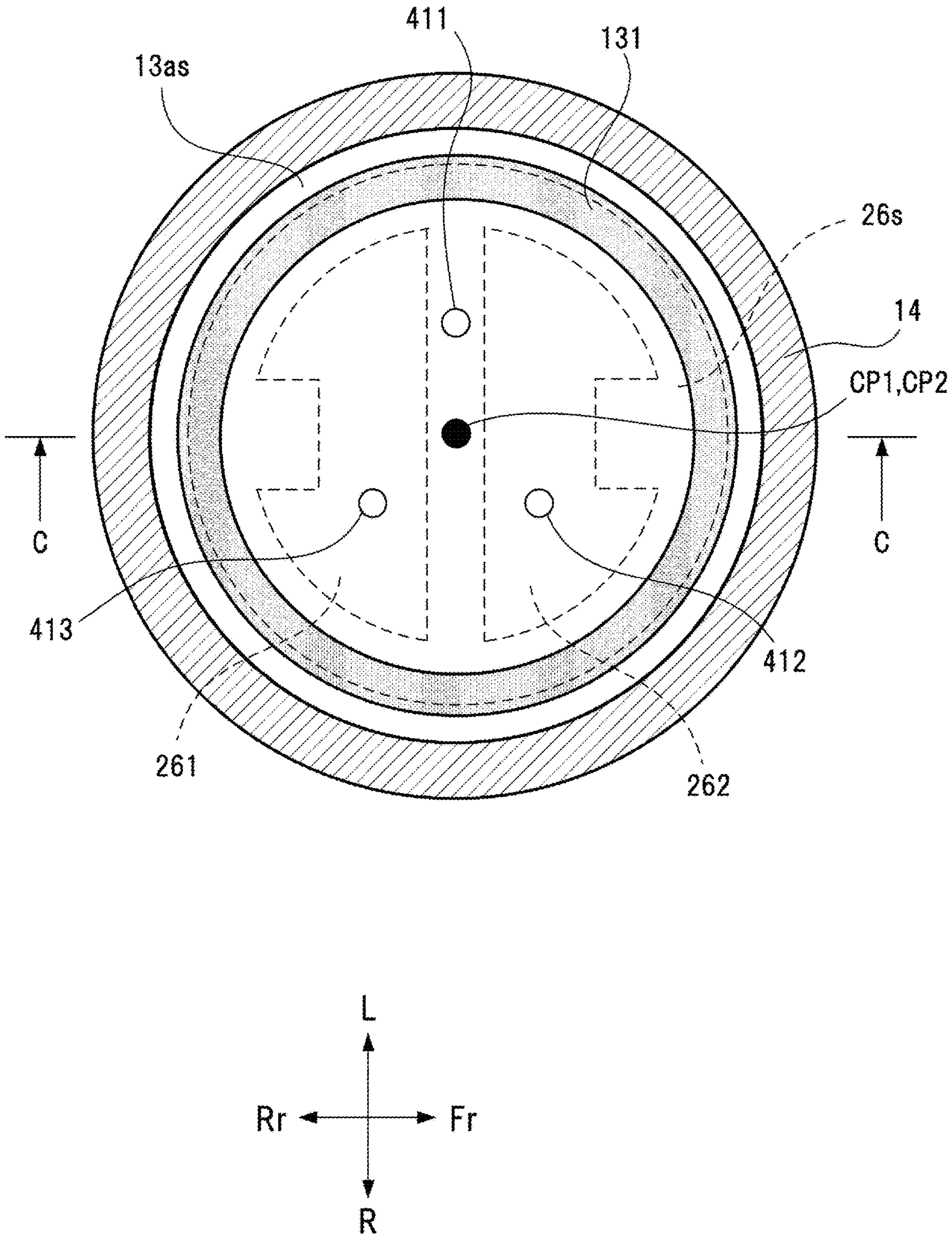
FIG. 14 is a schematic cross-sectional view taken along line B-B in FIG. 13.
Figure 15:
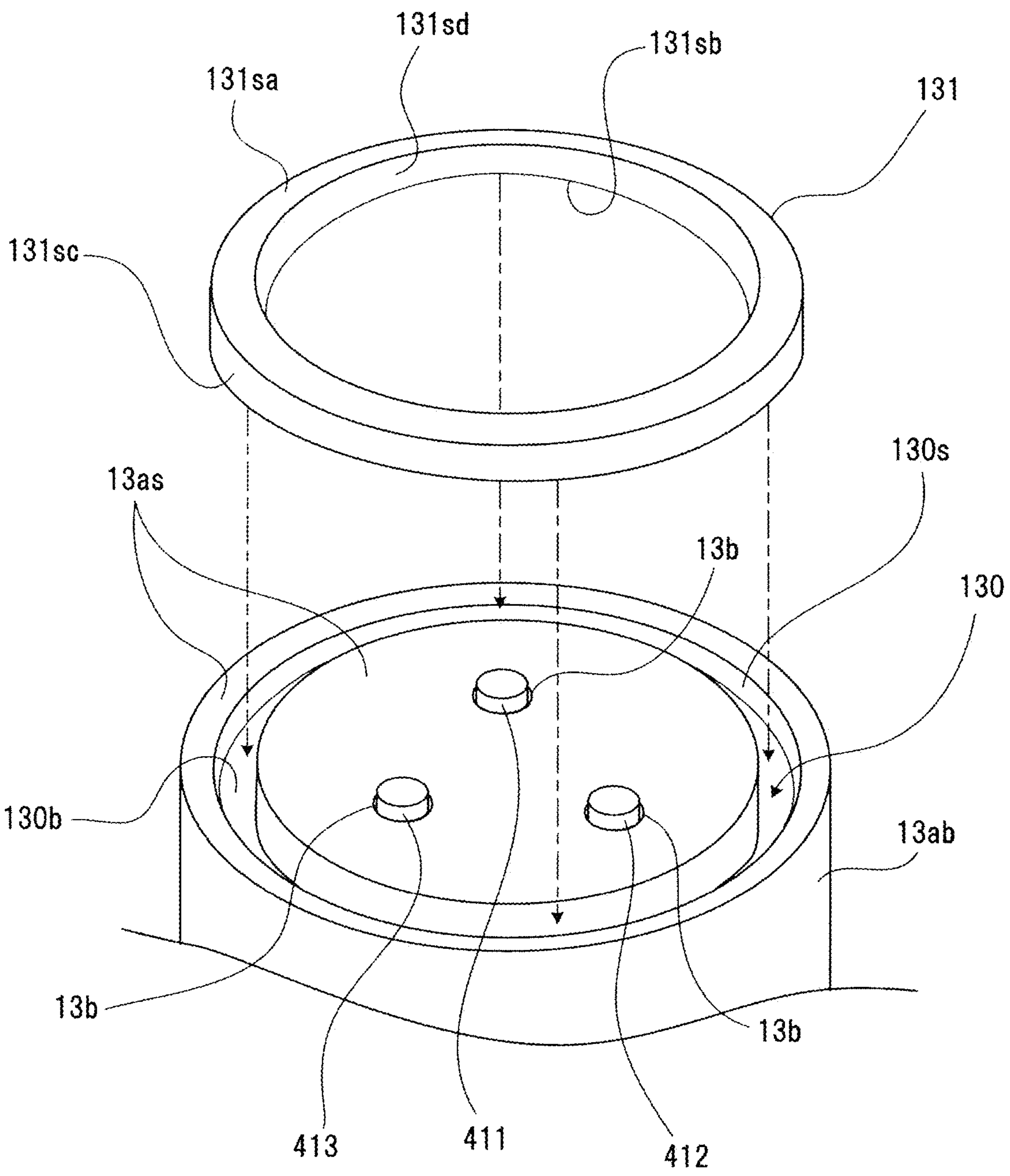
FIG. 15 is an exploded perspective view schematically showing a bottom portion of the cartridge accommodating portion in FIG. 13.

FIG. 14 is a schematic cross-sectional view taken along line B-B in FIG. 13. FIG. 15 is an exploded perspective view schematically showing the bottom wall portion **13*ab* of the cartridge accommodating portion CS in FIG. 13**.

As shown in FIG. 15, an annular recess 130 having a shape along an outer peripheral edge of the bottom wall portion **13*ab* is formed in the bottom surface 13*as* of the cartridge accommodating portion CS. The annular recess 130 is formed so as to surround a region in which the through hole 13*b* through which each of the protruding electrodes 411, 412, and 413 penetrates is formed. The annular member 131 is arranged in a non-fixed state in the annular recess 130. The non-fixed state refers to a state different from a state in which the annular recess 130 and the annular member 131 are firmly fixed to each other by adhesion, press-fitting, or the like, and refers to a state in which the annular member 131 can be removed from the annular recess 130. The annular member 131 is fitted into the annular recess 130 in such a state that the annular member 131 can rotate in the annular recess 130** if a strong force is applied in a circumferential direction thereof.

The annular member 131 is a flexible member made of a soft material such as urethane, silicon, resin, or rubber. The annular member 131 is implemented by a member having sufficiently lower rigidity than rigidity of the lower end portion 26 of the first cartridge 20. A coefficient of static friction between the surface **26*s* of the lower end portion 26 of the first cartridge 20 and the annular member 131 has a large value such that it suppress the first cartridge 20** being rotated inside the cartridge accommodating portion CS.

As shown in FIG. 14, an inner diameter of the annular member 131 is smaller than a diameter of the first cartridge 20, and the annular member 131 is configured to be capable of coming into contact with the surface 26*s* of the first cartridge 20 over the circumferential direction. In addition, a height of the annular member 131 in the up-down direction is preferably larger than a depth of the annular recess 130 in the up-down direction. It is more preferable that an upper surface of the annular member 131 is located between tip ends of the protruding electrodes 411, 412, 413 and the bottom surface 13*as* of the cartridge accommodating portion CS.

As described above, in the cartridge accommodating portion CS shown in FIGS. 14 and 15, the annular member 131 is embedded in the bottom wall portion 13*ab* in a state of being exposed in the cartridge accommodating portion CS. Therefore, even if a force that rotates the first cartridge 20 in the circumferential direction is applied in a state in which the first cartridge 20 is accommodated in the cartridge accommodating portion CS, rotation of the first cartridge 20 due to the force is suppressed by a frictional force between the annular member 131 and the first cartridge 20. By suppressing the rotation of the first cartridge 20 in this way, it is possible to prevent wear of the first cartridge 20 and the cartridge accommodating portion CS caused by friction.

In addition, since the rotation of the first cartridge 20 is suppressed, short-circuiting is prevented, and safety can thus be improved. For example, in the state shown in FIG. 8, the first cartridge 20 is energized using, for example, the protruding electrode 411 and the protruding electrode 412. When the first cartridge 20 rotates and the protruding electrode 412 and the plate electrode 261 come into contact with each other during the energization, a short circuit occurs. By preventing the rotation of the first cartridge 20, occurrence of such a short circuit can be prevented.

In addition, in the cartridge accommodating portion CS shown in FIGS. 14 and 15, the annular member 131 is arranged in a state of not being fixed to the bottom wall portion 13*ab* of the cartridge accommodating portion CS. Therefore, a gap is formed between the annular member 131 and the bottom wall portion 13*ab* of the cartridge accommodating portion CS. The aerosol source 22 leaking from the first cartridge 20 can be collected by a capillary force due to the gap. As a result, the aerosol source 22 can be prevented from entering a region where the protruding electrodes and the plate electrodes are arranged, and durability and safety can thus be improved.

In FIGS. 14 and 15, the annular member 131 has the function of suppressing the rotation of the first cartridge 20. However, any configuration may be used as long as a frictional force can be generated between the bottom wall portion 13*ab* and the first cartridge 20. For example, instead of the annular member 131, a plurality of arc-shaped flexible members may be arranged in the annular recess 130.

(Preferred Embodiments of Cartridge Accommodating Portion According to Fourth Modification)

Hereinafter, preferred embodiments of the cartridge accommodating portion CS shown in FIGS. 14 and 15 will be described. The preferred embodiments described below can be combined as appropriate.

It is preferable that a part or all of a surface (an upper surface 131*sa* (see FIG. 15)) on the first cartridge 20 side of the annular member 131 is an uneven surface. With this configuration, the coefficient of static friction between the annular member 131 and the first cartridge 20 can be further increased, and thus an effect of suppressing the rotation of the first cartridge 20 can be enhanced.

It is preferable that a part or all of a surface (a lower surface 131*sb* (see FIG. 15)) on the bottom wall portion 13*ab* side of the annular member 131 is an uneven surface. With this configuration, a coefficient of static friction between the annular member 131 and a bottom surface 130*b* of the annular recess 130 can be increased, and thus the annular member 131 can be prevented from rotating. In addition, the capillary force can be increased by the unevenness of the lower surface 131*sb* of the annular member 131, and thus the effect of collecting the aerosol source 22 can be improved.

It is preferable that a part or all of the bottom surface 130*b* of the annular recess 130 is an uneven surface. With this configuration, the coefficient of static friction between the annular member 131 and the bottom surface 130*b* can be increased, and thus the annular member 131 can be prevented from rotating. In addition, the capillary force can be increased by the unevenness of the bottom surface 130*b*, and thus the effect of collecting the aerosol source 22 can be improved.

Figure 16:
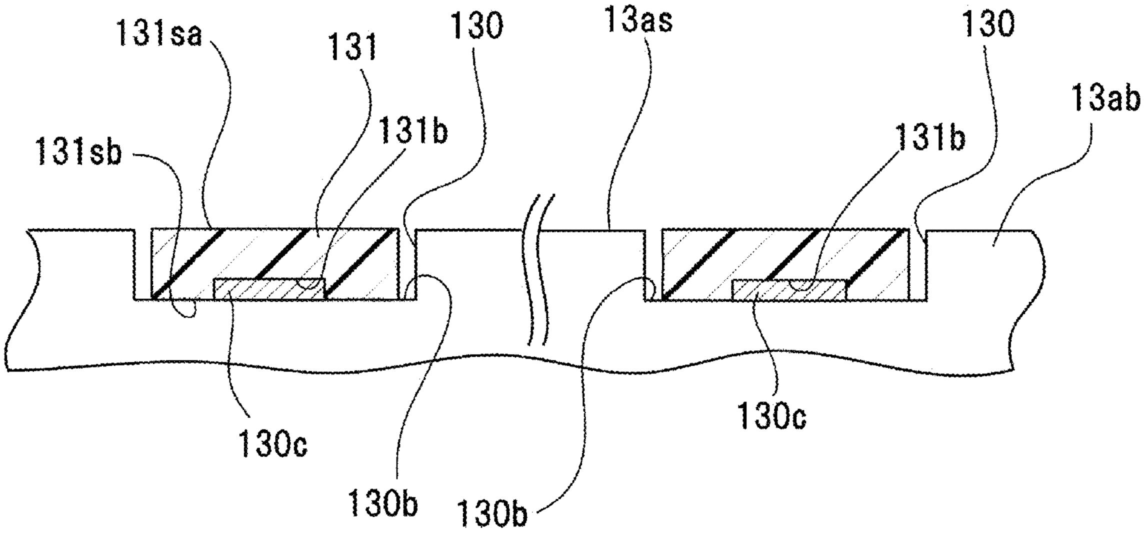
FIG. 16 is a schematic cross-sectional view showing a modification of a cross section taken along line C-C in FIG. 14.

FIG. 16 is a schematic cross-sectional view showing a modification of a cross section taken along line C-C in FIG. 14. In this modification, at least one recess 131*b* is formed in the lower surface 131*sb* of the annular member 131, and a protrusion 130*c* that engages with each recess 131*b* of the annular member 131 is formed on the bottom surface 130*b* of the annular recess 130, which is different from the cartridge accommodating portion CS in FIGS. 14 and 15. Each of the recess 131*b* and the protrusion 130*c* that engages with the recess 131*b* has, for example, a cylindrical shape or a rectangular parallelepiped shape.

According to the configuration in FIG. 16, the annular member 131 and the bottom wall portion 13*ab* of the cartridge accommodating portion CS are engaged with each other by the recess 131*b* and the protrusion 130*c*. Therefore, rotation of the annular member 131 can be suppressed. The same effect can also be obtained by forming a protrusion on the lower surface 131*sb* of the annular member 131 and forming a recess that engages with the protrusion in the bottom surface 130*b* of the annular recess 130. In order to increase an engagement force, it is preferable that a plurality of pairs of the recess 131*b* and the protrusion 130*c* are arranged side by side in the circumferential direction.

Figure 17:
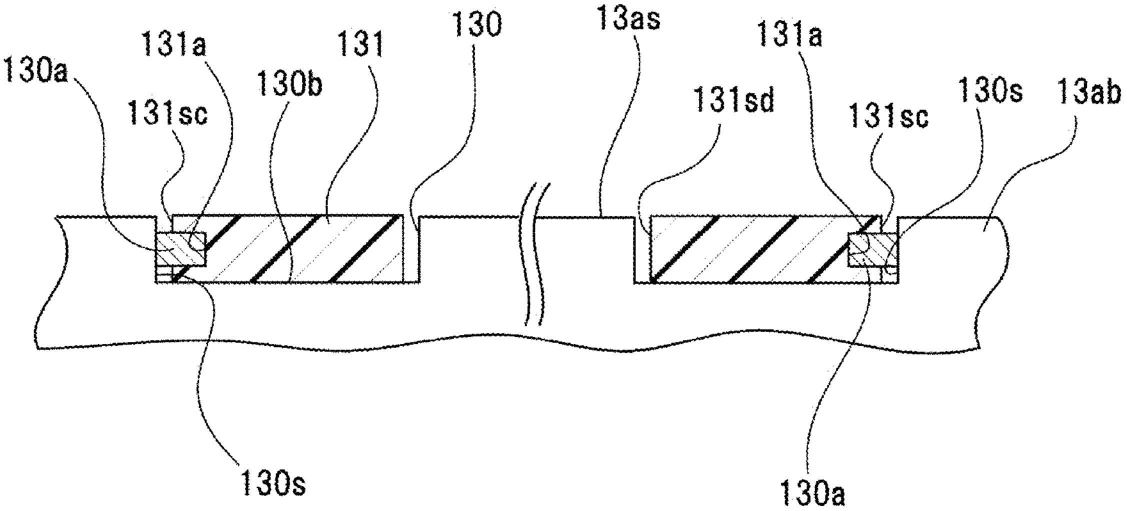
FIG. 17 is a schematic cross-sectional view showing another modification of the cross section taken along line C-C in FIG. 14.

FIG. 17 is a schematic cross-sectional view showing another modification of the cross section taken along line C-C in FIG. 14. In this modification, at least one recess 131*a* is formed in an outer peripheral side surface 131*sc* of the annular member 131, and a protrusion 130*a* that engages with each recess 131*a* of the annular member 131 is formed in the annular recess 130 on a wall surface 130*s* facing the outer peripheral side surface 131*sc*, which is different from the cartridge accommodating portion CS in FIGS. 14 and 15. Each of the recess 131*a* and the protrusion 130*a* that engages with the recess 131*a* has, for example, a cylindrical shape, a rectangular parallelepiped shape or an annular shape.

According to the configuration in FIG. 17, the annular member 131 and the wall surface 130*s* of the cartridge accommodating portion CS are engaged with each other by the recess 131*a* and the protrusion 130*a*. Therefore, the annular member 131 can be restricted from moving in the up-down direction. Therefore, it is possible to prevent the annular member 131 from being lifted by the aerosol source 22 collected between the annular member 131 and the bottom surface 130*b* of the annular recess 130.

The same effect can also be obtained by forming a protrusion on the outer peripheral side surface 131*sc* of the annular member 131 and forming a recess that engages with the protrusion in the wall surface 130*s* of the annular recess 130. In order to effectively prevent the annular member 131 from being lifted, it is preferable that each of the recess 131*a* and the protrusion 130*a* has an annular shape along the circumferential direction.

In addition, a protrusion or a recess may be formed on an inner peripheral side surface 131*sd* of the annular member 131, and a recess or a protrusion that engages with the protrusion or the recess may be provided on a wall surface, which faces the inner peripheral side surface 131*sd*, of the annular recess 130. With this configuration, it is still possible to prevent the annular member 131 from being lifted.

In the aerosol inhaler 1 according to the embodiments and the modifications thereof described above, the first cartridge 20 is provided with two electrodes (plate electrodes 261 and 262). However, the number of electrodes provided in the first cartridge 20 is not limited to two.

For example, a heater configured to heat the fragrance source 31 may be added to the first cartridge 20, and a total of four electrodes, that is, two electrodes configured to energize the heater and two electrodes configured to energize the load 21, may be provided in the first cartridge 20. Alternatively, two heaters configured to heat the aerosol source 22 may be provided in the first cartridge 20, and a total of four electrodes configured to energize each of the two heaters may be provided in the first cartridge 20.

In the case of these configurations, the number of protruding electrodes provided in the cartridge accommodating portion CS may be more than four, and may be five or more. In this way, regardless of the rotation position of the first cartridge 20, the electrodes provided in the second electrode portion are brought into contact with the electrodes provided in the first electrode portion, and the two heaters of the first cartridge 20 can be individually energized.

In the aerosol inhaler 1, on the surface 26*s* of the lower end portion 26 of the first cartridge 20, it is preferable that at least a portion of a region that can come into contact with the annular member 131 is an uneven surface. In this way, the effect of suppressing the rotation of the annular member 131 can be enhanced, and the capillary force can be increased.

In the above description, an upper end opening portion of the cartridge accommodating portion CS is closed by the second cartridge 30. However, for example, the second cartridge 30 may be installed to the power supply unit case 11 of the aerosol inhaler 1 in FIG. 1 from an upper end surface side, and the first cartridge 20 may be installed to the power supply unit case 11 from a lower end surface side. In this case, after the first cartridge 20 is inserted into the cartridge holder 14, for example, a lid portion provided on the lower end surface of the power supply unit case 11 is closed so as to close a lower end opening portion of the cartridge holder 14. In this configuration, for example, the second electrode portion may be provided on the lid portion, and the first electrode portion and the second electrode portion may be electrically connected to each other when the lid portion is closed. In this configuration, the cartridge holder 14 and the lid portion constitute an accommodating portion that accommodates the first cartridge 20.

In the present specification, at least the following matters are described. Although corresponding constituent elements or the like in the above embodiments are shown in parentheses, the present disclosure is not limited thereto.

(1) A power supply unit (power supply unit 10) of an aerosol generating device (aerosol inhaler 1), including: an accommodating portion (cartridge accommodating portion CS) with a bottom and cylindrical shape, which is configured to accommodate a columnar cartridge (first cartridge 20) that stores an aerosol source (aerosol source 22) in a state in which the cartridge is rotatable 360 degrees in a circumferential direction of the cartridge, in which a rotation suppressing portion (annular member 131) configured to generate a frictional force between the cartridge and the rotation preventing portion so as to suppress rotation of the cartridge in the circumferential direction is provided on a bottom portion (bottom wall portion 13*ab*) of the accommodating portion.

According to (1), it is possible to, by a function of the rotation preventing portion, suppress slight rotation of the cartridge in the accommodating portion due to an impact, vibration, or the like applied to the power supply unit. By suppressing the rotation of the cartridge, wear of the cartridge and the accommodating portion can be suppressed. In addition, when the cartridge and the bottom portion of the accommodating portion are electrically connected to each other, a short circuit caused by the rotation of the cartridge can be prevented.

(2) The power supply unit of an aerosol generating device according to (1), in which the rotation suppressing portion is implemented by an annular member (annular member 131) along an outer periphery of the bottom portion.

According to (2), since the rotation suppressing portion is implemented by the annular member, the frictional force generated between the cartridge and the rotation preventing portion when the cartridge rotates can be increased. Therefore, the effect of suppressing the rotation of the cartridge can be enhanced.

(3) The power supply unit of an aerosol generating device according to (2), in which the annular member is implemented by a flexible member.

According to (3), the function of the rotation preventing portion can be easily implemented, and a manufacturing cost can be reduced.

(4) The power supply unit of an aerosol generating device according to (3), in which at least a part of a surface (upper surface 131*sa*) on the cartridge side of the annular member is an uneven surface.

According to (4), the frictional force with respect to the cartridge can be increased by the uneven surface of the annular member. Therefore, the effect of suppressing the rotation of the cartridge can be enhanced.

(5) The power supply unit of an aerosol generating device according to any one of (2) to (4), in which the annular member is arranged in a state of being not fixed to the bottom portion of the accommodating portion.

According to (5), a gap is formed between the annular member and the bottom portion of the accommodating portion. Therefore, the aerosol source leaking from the cartridge can be collected by a capillary force due to the gap.

(6) The power supply unit of an aerosol generating device according to (5), in which at least a part of a surface (lower surface 131*sb*), which is located on the side of the bottom portion of the accommodating portion, of the annular member is an uneven surface.

According to (6), rotation of the annular member can be prevented by the uneven surface on the bottom portion side of the annular member. In addition, the effect of collecting the aerosol source by the capillary force is improved by the uneven surface.

(7) The power supply unit of an aerosol generating device according to (5) or (6), in which a first engagement recess (recess 131*b*) is formed in the surface on the bottom portion side of the annular member, and a protrusion (protrusion 130*c*) configured to engage with the first engagement recess of the annular member is formed on the bottom portion of the accommodating portion in a region facing the annular member.

According to (7), since the annular member and the bottom portion of the accommodating portion are engaged with each other by the first engagement recess and the protrusion, the rotation of the annular member can be suppressed.

(8) The power supply unit of an aerosol generating device according to (5) or (6), in which a first engagement protrusion is formed on the surface on the bottom portion side of the annular member, and a recess configured to engage with the first engagement protrusion of the annular member is formed on the bottom portion of the accommodating portion in a region facing the annular member.

According to (8), since the annular member and the bottom portion of the accommodating portion are engaged with each other by the first engagement protrusion and the recess, the rotation of the annular member can be suppressed.

(9) The power supply unit of an aerosol generating device according to any one of (5) to (8), in which a second engagement recess (recess 131*a*) is provided in a peripheral side surface (outer peripheral side surface 131*sc* or inner peripheral side surface) of the annular member, and the accommodating portion is provided with a protrusion (protrusion 130*a*) configured to engage with the second engagement recess.

According to (9), movement of the annular member in an axial direction can be restricted by an engagement force between the second engagement recess and the protrusion of the accommodating portion. Therefore, the annular member can be prevented by the engagement force from being lifted by the aerosol source collected between the annular member and the accommodating portion.

(10) The power supply unit of an aerosol generating device according to any one of (5) to (8), in which a second engagement protrusion is provided on a peripheral side surface (outer peripheral side surface 131*sc* or inner peripheral side surface) of the annular member, and the accommodating portion is provided with a recess configured to engage with the second engagement protrusion.

According to (10), the movement of the annular member in the axial direction can be restricted by an engagement force between the second engagement protrusion and the recess of the accommodating portion. Therefore, the annular member can be prevented by the engagement force from being lifted by the aerosol source collected between the annular member and the accommodating portion.

(11) An aerosol generating device including: the power supply unit of an aerosol generating device according to any one of (1) to (10); and the cartridge, in which unevenness is formed on an end surface (lower end surface 26), which is located on a bottom portion side of the accommodating portion, of the cartridge.

According to (11), it is possible to generate a frictional force between the cartridge and the accommodating portion by the unevenness of the cartridge. The cartridge can be firmly prevented from rotating in the accommodating portion by both this frictional force and the frictional force generated by the rotation preventing portion.

Although various embodiments have been described above with reference to the drawings, it is needless to say that the present disclosure is not limited to these examples. It is apparent that those skilled in the art can conceive of various modifications and alterations within the scope described in the claims, and it is understood that such modifications and alterations naturally fall within the technical scope of the present disclosure. In addition, the respective constituent elements in the above-described embodiments may be combined as desired without departing from the gist of the invention.

The invention claimed is:

1. A power supply unit of an aerosol generating device, comprising:

an accommodating portion with a bottom and cylindrical shape, which is configured to accommodate a columnar cartridge that stores an aerosol source in a state in which the columnar cartridge is rotatable 360 degrees in a circumferential direction of the cartridge, wherein a rotation suppressing portion configured to generate a frictional force between the columnar cartridge and the rotation suppressing portion so as to suppress rotation of the columnar cartridge in the circumferential direction is provided on a bottom portion of the accommodating portion, and the rotation suppressing portion is implemented by an annular member along an outer periphery of the bottom portion.

2. The power supply unit of an aerosol generating device according to claim 1, wherein the annular member is implemented by a flexible member.

3. The power supply unit of the aerosol generating device according to claim 2, wherein at least a part of a surface on the columnar cartridge side of the annular member is an uneven surface.

4. The power supply unit of an aerosol generating device according to claim 1, wherein the annular member is arranged in a state of being not fixed to the bottom portion of the accommodating portion.

5. The power supply unit of an aerosol generating device according to claim 4, wherein at least a part of a surface on a bottom portion side of the annular member is an uneven surface.

6. The power supply unit of an aerosol generating device according to claim 4, wherein a first engagement recess is formed in the surface on a bottom portion side of the annular member, and a protrusion configured to engage with the first engagement recess of the annular member is formed on the bottom portion of the accommodating portion in a region facing the annular member.

7. The power supply unit of an aerosol generating device according to claim 4, wherein a first engagement protrusion is formed on the surface on a bottom portion side of the annular member, and a recess configured to engage with the first engagement protrusion of the annular member is formed in the bottom portion of the accommodating portion in a region facing the annular member.

8. The power supply unit of an aerosol generating device according to claim 4, wherein a second engagement recess is provided in a peripheral side surface of the annular member, and the accommodating portion is provided with a protrusion configured to engage with the second engagement recess.

9. The power supply unit of an aerosol generating device according to claim 4, wherein a second engagement protrusion is provided on a peripheral side surface of the annular member, and the accommodating portion is provided with a recess configured to engage with the second engagement protrusion.

10. An aerosol generating device comprising: the power supply unit of an aerosol generating device according to claim 1; and the columnar cartridge, wherein unevenness is formed on an end surface, which is located on a bottom portion side of the accommodating portion, of the columnar cartridge.

11. A power supply configuration for an aerosol generating device, the power supply configuration comprising:

an accommodating portion having a bottom and a cylindrical shape, the accommodating portion including a cavity that receives a cartridge containing an aerosol source, the cavity shaped to allow 360-degree rotation of the cartridge; and an annular member located on the bottom of the accommodating portion, the annular member configured to generate a frictional force against the cartridge to inhibit circumferential rotation by the cartridge.

12. The power supply configuration of claim 11, wherein the annular member comprises a flexible material.

13. The power supply configuration of claim 12, wherein at least a portion of a surface of the annular member facing the cartridge is uneven.

14. The power supply configuration of claim 11, wherein the annular member is not fixed to the bottom of the accommodating portion.

15. The power supply configuration of claim 14, wherein at least a portion of a surface of the annular member facing the bottom of the accommodating portion is uneven.

16. The power supply configuration of claim 14, wherein an engagement recess is formed in a surface of the annular member facing the bottom of the accommodating portion, and a protrusion formed on the bottom of the accommodating portion in a region facing the annular member is configured to engage with the engagement recess.

17. The power supply configuration of claim 14, wherein an engagement protrusion is formed on a surface of the annular member facing the bottom of the accommodating portion, and a recess formed in the bottom of the accommodating portion in a region facing the annular member is configured to engage with the engagement protrusion.

18. The power supply configuration of claim 14, wherein an engagement recess is provided in a peripheral side surface of the annular member, and the accommodating portion comprises a protrusion configured to engage with the engagement recess.

19. The power supply configuration of claim 14, wherein an engagement protrusion is provided on a peripheral side surface of the annular member, and the accommodating portion comprises a recess configured to engage with the engagement protrusion.

* * * * *